United States Patent
Lee

(10) Patent No.: US 8,067,623 B2
(45) Date of Patent: Nov. 29, 2011

(54) RING OPENING CROSS-METATHESIS REACTION OF CYCLIC OLEFINS WITH SEED OILS AND THE LIKE

(75) Inventor: Choon Woo Lee, La Canada, CA (US)

(73) Assignee: Elevance Renewable Sciences, Inc., Boilingbrook, IL (US)

( * ) Notice: Subject to any disclaimer, the term of this patent is extended or adjusted under 35 U.S.C. 154(b) by 1021 days.

(21) Appl. No.: 11/827,937

(22) Filed: Jul. 12, 2007

(65) Prior Publication Data
US 2008/0064891 A1 Mar. 13, 2008

Related U.S. Application Data

(60) Provisional application No. 60/853,300, filed on Jul. 12, 2006.

(51) Int. Cl.
*C07C 51/00* (2006.01)
*C07C 67/00* (2006.01)

(52) U.S. Cl. .......................... 554/124; 560/128

(58) Field of Classification Search .............. 554/124; 560/128
See application file for complete search history.

(56) References Cited

U.S. PATENT DOCUMENTS

| | | |
|---|---|---|
| 2,619,422 A | 11/1952 | Whiting |
| 3,448,178 A | 6/1969 | Flanagan |
| 3,896,053 A | 7/1975 | Broecker et al. |
| 4,634,606 A | 1/1987 | Skogg |
| 5,043,485 A | 8/1991 | Fleckenstein et al. |
| 5,312,940 A | 5/1994 | Grubbs et al. |
| 5,506,363 A | 4/1996 | Grate et al. |
| 5,639,526 A | 6/1997 | Kotsiopoulos et al. |
| 5,700,516 A | 12/1997 | Sandvick et al. |
| 5,710,298 A | 1/1998 | Grubbs et al. |
| 5,728,785 A | 3/1998 | Grubbs et al. |
| 5,728,917 A | 3/1998 | Grubbs et al. |
| 5,734,070 A | 3/1998 | Tacke et al. |
| 5,750,815 A | 5/1998 | Grubbs et al. |
| 5,811,515 A | 9/1998 | Grubbs et al. |
| 5,831,108 A | 11/1998 | Grubbs et al. |

(Continued)

FOREIGN PATENT DOCUMENTS

DE 19956226 5/2001

(Continued)

OTHER PUBLICATIONS

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

(Continued)

*Primary Examiner* — Deborah D Carr
(74) *Attorney, Agent, or Firm* — Brinks Hofer Gilson & Lione

(57) ABSTRACT

This invention relates generally to olefin metathesis, and more particularly relates to the ring-opening, ring insertion cross-metathesis of cyclic olefins with internal olefins such as seed oils and the like. In one embodiment, a method is provided for carrying out a catalytic ring-opening cross-metathesis reaction, comprising contacting at least one olefinic substrate with at least one cyclic olefin as a cross metathesis partner, in the presence of a ruthenium alkylidene olefin metathesis catalyst under conditions effective to allow ring insertion cross metathesis whereby the cyclic olefin is simultaneously opened and inserted into the olefinic substrate. The invention has utility in the fields of catalysis, organic synthesis, and industrial chemistry.

37 Claims, 2 Drawing Sheets

U.S. PATENT DOCUMENTS

| | | | |
|---|---|---|---|
| 5,849,851 A | 12/1998 | Grubbs et al. |
| 5,880,231 A | 3/1999 | Grubbs et al. |
| 5,917,071 A | 6/1999 | Grubbs et al. |
| 5,922,863 A | 7/1999 | Grubbs et al. |
| 5,939,504 A | 8/1999 | Woodson, Jr. et al. |
| 5,969,170 A | 10/1999 | Grubbs et al. |
| 5,977,393 A | 11/1999 | Grubbs et al. |
| 6,020,443 A | 2/2000 | Woodson, Jr. et al. |
| 6,040,363 A | 3/2000 | Warner et al. |
| 6,063,144 A | 5/2000 | Calzada et al. |
| 6,080,826 A | 6/2000 | Grubbs et al. |
| 6,107,420 A | 8/2000 | Grubbs et al. |
| 6,169,198 B1 | 1/2001 | Fischer et al. |
| 6,197,894 B1 | 3/2001 | Sunaga et al. |
| 6,211,315 B1 | 4/2001 | Larock et al. |
| 6,214,918 B1 | 4/2001 | Johnson et al. |
| 6,215,019 B1 | 4/2001 | Pederson et al. |
| 6,224,641 B1 | 5/2001 | Matzat et al. |
| 6,255,375 B1 | 7/2001 | Michelman |
| 6,262,153 B1 | 7/2001 | Webster et al. |
| 6,281,163 B1 | 8/2001 | Van Dijk |
| 6,284,007 B1 | 9/2001 | Tao |
| 6,284,852 B1 | 9/2001 | Lynn et al. |
| 6,306,988 B1 | 10/2001 | Grubbs et al. |
| 6,310,121 B1 | 10/2001 | Woodson, Jr. et al. |
| 6,316,380 B1 | 11/2001 | Nolan et al. |
| 6,323,296 B1 | 11/2001 | Warner et al. |
| 6,376,690 B1 | 4/2002 | Grubbs et al. |
| 6,409,875 B1 | 6/2002 | Giardello et al. |
| 6,410,110 B1 | 6/2002 | Warner et al. |
| 6,410,666 B1 | 6/2002 | Grubbs et al. |
| 6,426,419 B1 | 7/2002 | Grubbs et al. |
| 6,433,101 B1 | 8/2002 | Woodson et al. |
| 6,465,590 B1 | 10/2002 | Maughon et al. |
| 6,503,285 B1 | 1/2003 | Murphy |
| 6,525,125 B1 | 2/2003 | Giardello et al. |
| 6,583,236 B1 | 6/2003 | Giardello et al. |
| 6,586,506 B2 | 7/2003 | Webster et al. |
| 6,599,334 B1 | 7/2003 | Anderson |
| 6,610,626 B2 | 8/2003 | Grubbs et al. |
| 6,613,910 B2 | 9/2003 | Grubbs et al. |
| 6,620,955 B1 | 9/2003 | Pederson et al. |
| 6,645,261 B2 | 11/2003 | Murphy et al. |
| 6,696,597 B2 | 2/2004 | Pederson et al. |
| 6,716,155 B2 | 4/2004 | Sleeter |
| 6,730,137 B2 | 5/2004 | Pesu et al. |
| 6,759,537 B2 | 7/2004 | Grubbs et al. |
| 6,770,104 B2 | 8/2004 | Murphy |
| 6,773,469 B2 | 8/2004 | Murphy |
| 6,794,534 B2 | 9/2004 | Grubbs et al. |
| 6,797,020 B2 | 9/2004 | Murphy |
| 6,803,429 B2 | 10/2004 | Morgan et al. |
| 6,818,586 B2 | 11/2004 | Grubbs et al. |
| 6,824,572 B2 | 11/2004 | Murphy |
| 6,838,489 B2 | 1/2005 | Bell et al. |
| 6,846,573 B2 | 1/2005 | Seydel |
| 6,884,859 B2 | 4/2005 | Grubbs et al. |
| 6,900,347 B2 | 5/2005 | Paulson et al. |
| 6,921,735 B2 | 7/2005 | Hoveyda et al. |
| 6,921,736 B1 | 7/2005 | Nolan et al. |
| 6,946,533 B2 | 9/2005 | Grubbs et al. |
| 6,962,729 B2 | 11/2005 | Tokas et al. |
| 6,987,154 B2 | 1/2006 | Choi et al. |
| 7,026,495 B1 | 4/2006 | Pederson et al. |
| 7,034,096 B2 | 4/2006 | Choi et al. |
| 7,041,864 B2 * | 5/2006 | Fong et al. ............ 585/646 |
| 7,109,348 B1 | 9/2006 | Nolan |
| 7,119,216 B2 | 10/2006 | Newman et al. |
| 7,128,766 B2 | 10/2006 | Murphy et al. |
| 7,176,336 B2 | 2/2007 | Maughon et al. |
| 7,192,457 B2 | 3/2007 | Murphy et al. |
| 7,205,424 B2 | 4/2007 | Nolan |
| 7,217,301 B2 | 5/2007 | Murphy et al. |
| 7,285,593 B1 | 10/2007 | Giardello et al. |
| 7,314,904 B2 | 1/2008 | Nadolsky et al. |
| 7,329,758 B1 | 2/2008 | Grubbs et al. |
| 7,365,140 B2 | 4/2008 | Piers et al. |
| 7,462,205 B2 | 12/2008 | Murphy |
| 7,507,854 B2 | 3/2009 | Lee et al. |
| 7,598,330 B2 | 10/2009 | Grubbs et al. |
| 7,622,590 B1 | 11/2009 | Nolan et al. |
| 7,812,185 B2 | 10/2010 | Burdett et al. |
| 2001/0051680 A1 | 12/2001 | Webster et al. |
| 2002/0095007 A1 | 7/2002 | Larock et al. |
| 2002/0157303 A1 | 10/2002 | Murphy et al. |
| 2003/0017431 A1 | 1/2003 | Murphy |
| 2003/0046860 A1 | 3/2003 | Tiffany et al. |
| 2003/0055262 A1 | 3/2003 | Grubbs et al. |
| 2003/0057599 A1 | 3/2003 | Murphy et al. |
| 2003/0061760 A1 | 4/2003 | Tao et al. |
| 2003/0091949 A1 | 5/2003 | Pesu et al. |
| 2003/0100776 A1 | 5/2003 | Grubbs et al. |
| 2003/0110683 A1 | 6/2003 | Murphy |
| 2003/0186035 A1 | 10/2003 | Cruce et al. |
| 2003/0198826 A1 | 10/2003 | Seydel |
| 2003/0207971 A1 | 11/2003 | Stuart, Jr. et al. |
| 2003/0236377 A1 | 12/2003 | Choi et al. |
| 2004/0047886 A1 | 3/2004 | Murphy et al. |
| 2004/0088907 A1 | 5/2004 | Murphy |
| 2004/0088908 A1 | 5/2004 | Murphy |
| 2004/0200136 A1 | 10/2004 | Tao et al. |
| 2004/0221503 A1 | 11/2004 | Murphy et al. |
| 2004/0221504 A1 | 11/2004 | Murphy |
| 2005/0014664 A1 | 1/2005 | Nadolsky et al. |
| 2005/0027136 A1 | 2/2005 | Toor et al. |
| 2005/0060927 A1 | 3/2005 | Murphy |
| 2005/0070750 A1 | 3/2005 | Newman et al. |
| 2005/0080301 A1 | 4/2005 | Maughon et al. |
| 2005/0123780 A1 | 6/2005 | Seydel |
| 2005/0154221 A1 | 7/2005 | Lysenko et al. |
| 2005/0158679 A1 | 7/2005 | Chen et al. |
| 2005/0261451 A1 | 11/2005 | Ung et al. |
| 2005/0269728 A1 | 12/2005 | Roos |
| 2006/0079704 A1 | 4/2006 | Lacombe et al. |
| 2006/0128912 A1 | 6/2006 | Piers et al. |
| 2006/0236593 A1 | 10/2006 | Cap |
| 2006/0272199 A1 | 12/2006 | Licciardello et al. |
| 2006/0272200 A1 | 12/2006 | Murphy et al. |
| 2007/0006522 A1 | 1/2007 | Tao |
| 2007/0039237 A1 | 2/2007 | Murphy et al. |
| 2007/0144058 A1 | 6/2007 | Chen et al. |
| 2007/0151480 A1 | 7/2007 | Bloom et al. |
| 2007/0282000 A1 | 12/2007 | Murphy et al. |
| 2008/0027194 A1 | 1/2008 | Schrodi |
| 2008/0064891 A1 | 3/2008 | Lee |
| 2009/0217568 A1 | 9/2009 | Murphy et al. |

FOREIGN PATENT DOCUMENTS

| | | |
|---|---|---|
| EP | 1408064 A1 | 4/2004 |
| FR | 2878246 A1 | 5/2006 |
| JP | 56077243 | 6/1981 |
| JP | 09014574 | 1/1997 |
| SU | 1565872 | 5/1990 |
| WO | WO 96/04289 | 2/1996 |
| WO | WO 00/46565 | 8/2000 |
| WO | WO 01/36368 | 5/2001 |
| WO | WO 03/018905 | 3/2003 |
| WO | WO 03/057983 | 7/2003 |
| WO | WO 03/093215 | 11/2003 |
| WO | WO 03/104348 | 12/2003 |
| WO | WO 2004/033388 | 4/2004 |
| WO | WO 2004/062763 | 7/2004 |
| WO | WO 2004/083310 | 9/2004 |
| WO | WO 2005/026106 | 3/2005 |
| WO | WO 2005/042655 | 5/2005 |
| WO | WO 2005/080455 | 9/2005 |
| WO | WO 2006/052688 | 5/2006 |
| WO | WO 2006/076364 | 7/2006 |
| WO | WO 2007/002999 | 1/2007 |
| WO | WO 2007/081987 | 7/2007 |
| WO | WO 2007/103398 | 9/2007 |
| WO | WO 2008/046106 A2 | 4/2008 |
| WO | WO 2008/048522 A1 | 4/2008 |
| WO | WO 2008/063322 A2 | 5/2008 |

OTHER PUBLICATIONS

Baumann et al., "Natural Fats and Oils—Renewable Raw Materials for the Chemical Industry," Angewandte Chemie International Edition in English, vol. 27, 1988, pp. 41-62.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al. , "Drying Properties of Metathesized Soybean Oil," Journal of American Oil Chemists' Society, AOCS Press, vol. 74, No. 6, 1997, pp. 703-706.

Feuge et al., "1,3-Diolein and 1,3-Distearin Esters of Fumaric, Succinic and Adipic Acids," Journal of American Chemical Society, vol. 80, 1958, pp. 6338-6341.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

Refvik et al., "Ruthenium-Catalyzed Metathesis of Vegetable Oils," Journal of American Oil Chemists' Society, AOCS Press, vol. 76, No. 1, 1999, pp. 93-98.

Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.

Shorland, "Glycol Esters of Dibasic Acids. The Di-$\beta$-hydroxyethyl Esters," Journal of American Chemical Society, vol. 57, No. 1, 1935, pp. 115-116.

Tian et al., "Model Studies and the ADMET Polymerization of Soybean Oil," Journal of American Oil Chemists' Society, AOCS Press, vol. 79, No. 5, 2002, pp. 479-488.

Ward et al., "New Fat Products: Glyceride Esters of Adipic Acid," Journal of the Amiercan Oil Chemists' Society, vol. 36, 1959, pp. 667-671.

International Search Report and Written Opinion of the International Searching Authority for International Application No. PCT/US2006/000822, dated Jul. 14, 2006, 13 pages.

International Search Report for International Application No. PCT/US2007/015905, dated Apr. 23, 2008, 3 pages.

International Search Report and Written Opinion of the International Searching Authority for International Application No. PCT/US2007/00610, dated Oct. 11, 2007, 8 pages.

International Search Report and Written Opinion of the International Searching Authority for International Application No. PCT/US2007/005736, dated Aug. 8, 2007, 11 pages.

International Search Report and Written Opinion of the International Searching Authority for International Application No. PCT/US2007/005868, dated Nov. 9, 2007, 7 pages.

International Search Report for International Application No. PCT/US2007/015866, dated Nov. 26, 2007, 3 pages.

International Search Report for International Application No. PCT/US2007/016010, dated Mar. 11, 2008, 4 pages.

International Search Report for International Application No. PCT/US2007/021931, dated Apr. 11, 2008, 3 pages.

International Search Report for International Application No. PCT/US2007/021934, dated Jun. 17, 2008, 3 pages.

International Search Report for International Application No. PCT/US2007/021939, dated Feb. 18, 2008, 2 pages.

International Search Report and Written Opinion of the International Searching Authority for International Application No. PCT/US2008/009604, dated Oct. 27, 2008, 6 pages.

International Search Report and Written Opinion of the International Searching Authority for International Application No. PCT/US2008/009635, dated Oct. 27, 2008, 7 pages.

International Search Report for International Application No. PCT/US2008/065395, dated Sep. 29, 2008, 1 page.

International Search Report for International Application No. PCT/US2008/067025, dated Sep. 8, 2008, 1 page.

European Examination Report for counterpart European Application No. 07810390.0, dated May 19, 2010, 6 pages.

Patel et al., "High conversion and productive catalyst turnovers in cross-metathesis reactions of natural oils with 2-butene", Green Chemistry, 2006, vol. 8, pp. 450-454.

* cited by examiner

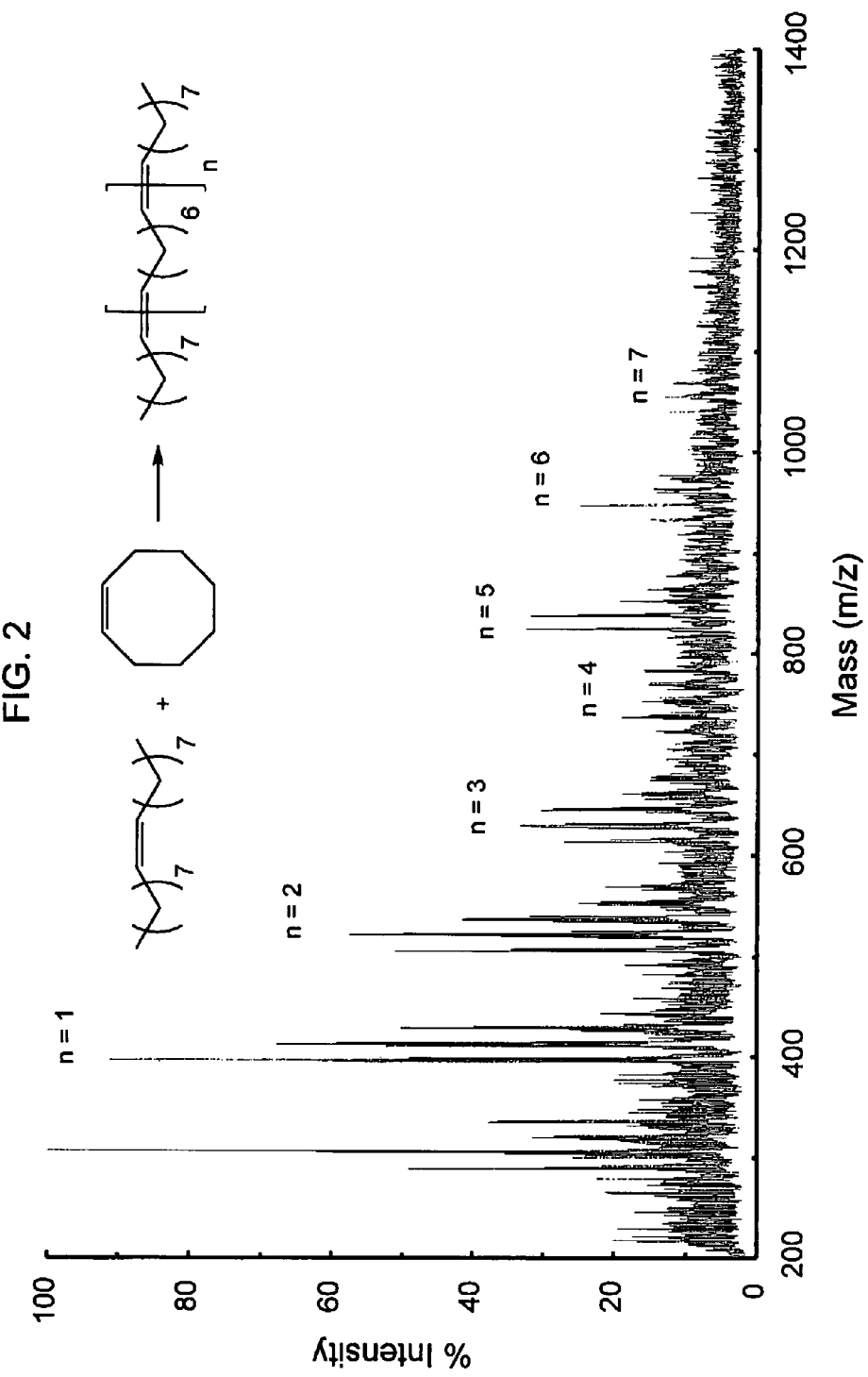

RING OPENING CROSS-METATHESIS REACTION OF CYCLIC OLEFINS WITH SEED OILS AND THE LIKE

RELATED APPLICATIONS

This application claims priority to U.S. Provisional Application Ser. No. 60/853,300, filed Jul. 12, 2006, the disclosure of which is incorporated herein by reference.

TECHNICAL FIELD

This invention relates generally to olefin metathesis, and more particularly relates to the ring-opening, ring insertion cross-metathesis of cyclic olefins with internal olefins such as seed oils and the like. The invention has utility in the fields of catalysis, organic synthesis, and industrial chemistry.

BACKGROUND

In the past 15 years, ruthenium olefin metathesis catalysts have firmly established olefin metathesis as a versatile and reliable synthetic technique for organic syntheses. The exceptionally wide scope of substrates and functional group tolerance makes olefin metathesis a valuable technique. In this application, the use of olefin cross metathesis to produce alpha-olefins is another example of the usefulness and the robustness of olefin metathesis technology. Compared to traditional synthetic organic techniques, olefin metathesis efficiently produces compounds that are otherwise hard to synthesize. Numerous man hours of research have resulted in the elucidation of many olefin metathesis reactions catalyzed by various transition metal complexes. In particular, certain ruthenium and osmium carbene compounds, known as "Grubbs' catalysts," have been identified as effective catalysts for olefin metathesis reactions such as, for example, cross-metathesis (CM), ring-closing metathesis (RCM), ring-opening metathesis (ROM), ring opening cross metathesis (ROCM), ring-opening metathesis polymerization (ROMP) or acyclic diene metathesis (ADMET) polymerization.

ROCM is a version of cross metathesis and historically has been underutilized mainly due the difficulty of controlling selectively. ROCM is an intermolecular exchange of a cyclic olefin and an acyclic olefin. In these instances, release of ring strain is the driving force for the reaction to proceed. A review of ROCM is provided by Schrader and Snapper in *Handbook of Metathesis*, Volume 2: Applications in Organic Synthesis (R. H. Grubbs Ed.), Wiley-VCH Verlag GmbH & Co. KGaA, Weinheim, 2003, pp 205-237.

Early ROCM examples were low yielding reactions with poor selectivities. Even with these shortcomings, ROCM has become an important fixture in metathesis history because ROCM was the key reaction used by Yves Chauvin to propose the currently accepted metathesis mechanism that bears his name, i.e. the Chauvin mechanism. Chauvin proposed the interchange of metal carbenes via a metallocyclobutane ring as an alternative mechanism to the then-accepted pair-wise mechanism for olefin cross metathesis. The metallocyclobutane mechanism was proposed based on the ROCM of cyclopentene with 2-pentene, shown in Scheme 1, which resulted in a statistical product distribution (1:2:1 of compounds 1, 2, and 3 respectively). In the pair-wise mechanism only compound 2 would be expected to form, at low conversions. Chauvin was rewarded for his insight and contributions to metathesis by sharing the 2005 Nobel Prize in Chemistry with Dr. Robert Grubbs and Dr. Richard Schrock.

Scheme 1. ROCM of Cyclopentene and 2-Pentene.

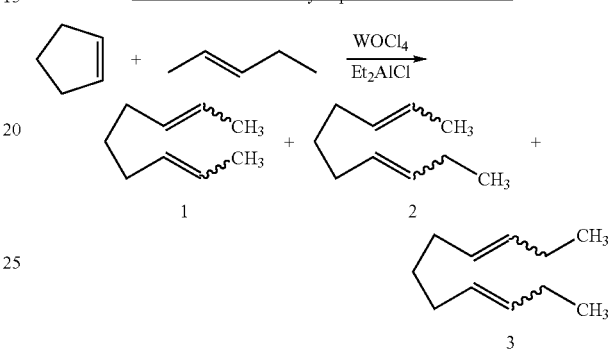

ROCM reactions using cyclododecene and methyl oleate or oleyl acetate have been reported. The reactions employed an ill-defined tungsten catalyst system to produce the ring inserted product, as shown in Scheme 2.

Scheme 2. ROCM with an ill-defined metathesis catalyst.

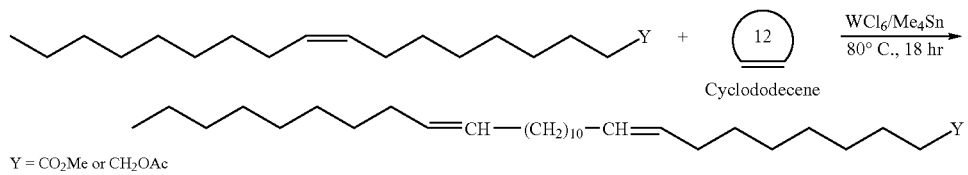

Y = CO₂Me or CH₂OAc

There is an ongoing need in the art for methods and systems that would allow ring insertion cross metathesis of cyclic olefins into internal olefins, e.g., seed oils and the like. This type of reaction would be useful in the preparation of various useful products, including, by way of example, chain-extended trialkylglycerides (TAGs) and chain-extended fatty acid methyl esters (FAMEs). An ideal such reaction could be implemented in the preparation of metathesis products useful as binders in urethane foams, latex pains, printing inks, and high melting point waxes.

SUMMARY OF THE DISCLOSURE

Accordingly, the invention is directed to addressing one or more of the aforementioned issues, and, in one embodiment, provides a method for carrying out a catalytic ring-opening cross-metathesis reaction. The method comprises contacting at least one olefinic substrate with at least one cyclic olefin as a cross metathesis partner, in the presence of a ruthenium alkylidene olefin metathesis catalyst. The at least one olefinic substrate is selected from: (i) an unsaturated fatty acid; (ii) an unsaturated fatty alcohol; (iii) an esterification product of an unsaturated fatty acid with an alcohol; and (iv) an esterification product of a saturated fatty acid with an unsaturated alcohol. The contacting is carried out under conditions effective to allow ring insertion cross metathesis whereby the cyclic olefin is simultaneously opened and inserted into the olefinic substrate.

In another embodiment, the invention provides a method for manufacturing a wax. The method comprises contacting at least one olefinic substrate with at least one cyclic olefin as a cross metathesis partner in the presence of a ruthenium alkylidene olefin metathesis catalyst. The at least one olefinic substrate is selected from: (i) an unsaturated fatty acid or derivative thereof; (ii) an unsaturated fatty alcohol or derivative thereof; (iii) an esterification product of an unsaturated fatty acid with an alcohol; and (iv) an esterification product of a saturated fatty acid with an unsaturated alcohol. The reaction is carried out under conditions effective to allow ring insertion cross metathesis whereby the cyclic olefin is simultaneously opened and inserted into the olefinic substrate to provide an olefinic product. The method further comprises optionally hydrogenating the olefinic product, wherein the hydrogenation may be partial or complete hydrogenation.

In a still further embodiment, the invention provides a method for carrying out a catalytic ring-opening cross-metathesis reaction. The method comprises contacting at least one olefinic substrate with at least one cyclic olefin functionalized with a functional group as a cross metathesis partner, in the presence of a ruthenium alkylidene olefin metathesis catalyst. The at least one olefinic substrate is selected from: (i) an unsaturated fatty acid; (ii) an unsaturated fatty alcohol; (iii) an esterification product of an unsaturated fatty acid with an alcohol; and (iv) an esterification product of a saturated fatty acid with an unsaturated alcohol. The contacting is carried out under conditions effective to allow ring insertion cross metathesis whereby the cyclic olefin is simultaneously opened and inserted into the olefinic substrate.

In a still further embodiment, the invention provides a method for carrying our a catalytic ring-opening cross metathesis reaction. The method comprises contacting at least one olefinic substrate with at least one cyclic olefin as a cross metathesis partner, in the presence of a ruthenium alkylidene olefin metathesis catalyst. The catalyst is present in an amount that is less than 1000 ppm relative to the olefinic substrate, and the at least one olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol.

In a further embodiment, the invention provides a reaction system for carrying out a catalytic ring-opening cross-metathesis reaction comprising at least one olefinic substrate, at least one cyclic olefin, and a ruthenium alkylidene olefin metathesis catalyst. The at least one olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol.

In a still further embodiment, the invention provides a reaction system for manufacturing a wax. The reaction system comprises at least one olefinic substrate, at least one cyclic olefin, and a ruthenium alkylidene olefin metathesis catalyst. The at least one olefinic substrate is selected from: (i) an unsaturated fatty acid; (ii) an unsaturated fatty alcohol; (iii) an esterification product of an unsaturated fatty acid with an alcohol; and (iv) an esterification product of a saturated fatty acid with an unsaturated alcohol.

In a still further embodiment, the invention provides a ring-opening cross-metathesis product prepared using any of the methods and reaction systems disclosed herein.

In a still further embodiment, the invention provides a chain-extended olefinic substrate formed by a catalytic ring-opening cross-metathesis reaction. The reaction comprises contacting: (a) at least one olefinic substrate selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol, with (b) at least one cyclic olefin as a cross metathesis partner, in the presence of (c) a ruthenium alkylidene olefin metathesis catalyst, under conditions effective to allow ring insertion cross metathesis whereby the cyclic olefin is simultaneously opened and inserted into the olefinic substrate to form the chain-extended olefinic substrate.

In a still further embodiment, the invention provides a kit of parts for carrying out a catalytic ring-opening cross metathesis reaction. The kit of parts comprises at least one olefinic substrate and a ruthenium alkylidene olefin metathesis catalyst. The at least one olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol. The kit of parts further comprises: (a) at least one cyclic olefin; or (b) instructions for adding a cyclic olefin to the at least one olefinic substrate.

In a still further embodiment, the invention provides a kit of parts for manufacturing a wax. The kit of parts comprises at least one olefinic substrate and a ruthenium alkylidene olefin metathesis catalyst. The at least one olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol. The kit of parts further comprises: (a) at least one cyclic olefin; or (b) instructions for adding a cyclic olefin to the at least one olefinic substrate. The kit of parts further comprises instructions for hydrogenating metathesis products.

BRIEF DESCRIPTION OF THE DRAWINGS

FIG. 2 is a MALDI-TOF spectrum of ROCM Product (n=1) from metathesis of 9C18 and COE

DETAILED DESCRIPTION OF THE DISCLOSURE

Terminology and Definitions

Figure 1:
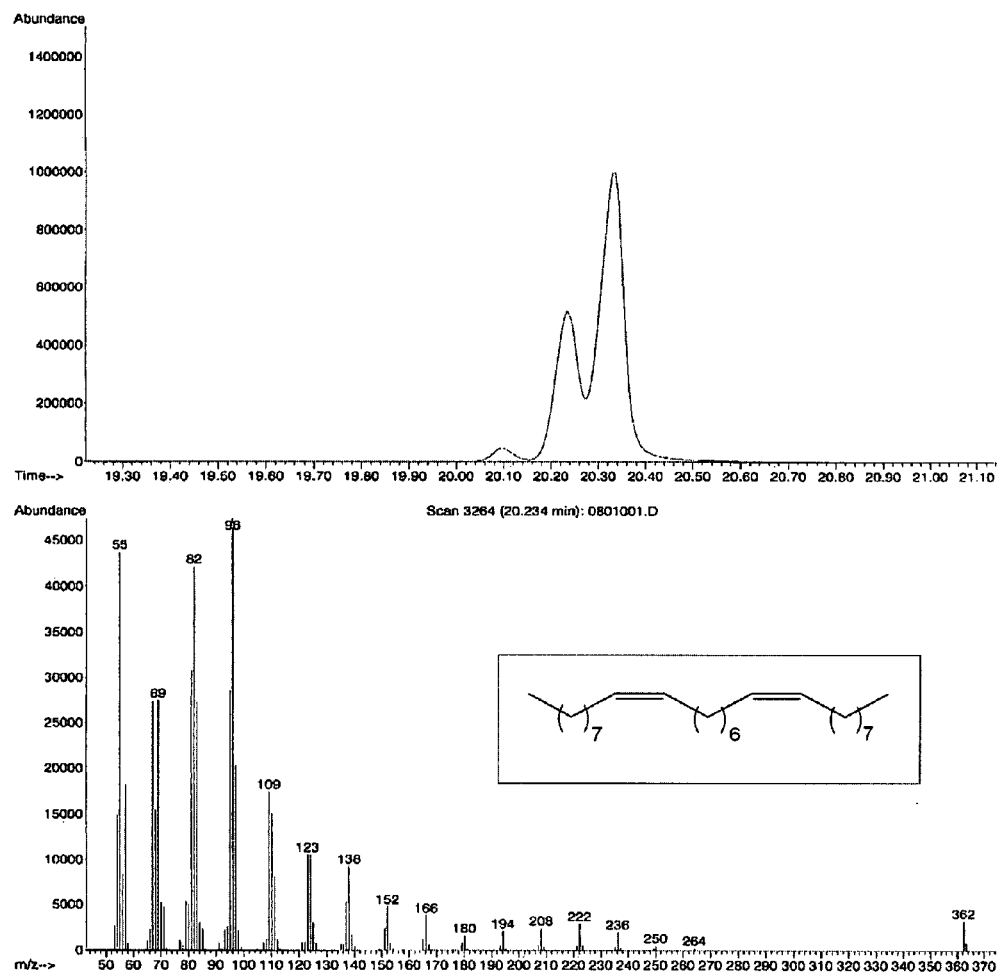
FIG. 1 is a typical GC-MS chromatogram of ROCM (n=1) products.

Unless otherwise indicated, the invention is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefin, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

A "kit of parts," as used herein, refers to a packaged collection of related components. Unless otherwise specified, the components of a kit of parts may be packaged individually or together in any combination.

A "reaction system," as used herein, refers to a functionally related group of components.

Methods and Compositions of the Disclosure I. First Embodiment Ring-Opening, Ring Insertion Cross-Metathesis Method of a Cyclic Olefin and an Internal Olefin as an Olefinic Substrate In a first embodiment, the invention provides an olefin cross-metathesis method in which the method involves ring-opening, ring insertion metathesis of at least one olefinic substrate and at least one cyclic olefin as the cross metathesis partner. The olefinic substrate is selected from (i) an unsaturated fatty acid or derivative thereof, (ii) an unsaturated fatty alcohol or derivative thereof, (iii) an esterification product of an unsaturated fatty acid with an alcohol, and (iv) an esterification product of a saturated fatty acid with an unsaturated alcohol. It will be appreciated that esterification products of an unsaturated fatty acid with an alcohol include many commercially available and industrially significant compositions, e.g., monoglycerides, diglycerides, and triglycerides such as may be found in seed oils and the like. The reaction is carried out catalytically, generally in the presence of a ruthenium alkylidene metathesis catalyst. In this embodiment, the reaction is carried out by contacting the at least one olefinic substrate with the cross metathesis partner, i.e., the at least one cyclic olefin, in the presence of the metathesis catalyst under reaction conditions effective to allow ring insertion cross metathesis whereby the cyclic olefin is simultaneously opened and inserted into the olefinic substrate.

The olefinic substrate is any olefinic substrate that is suitable for the metathesis methods disclosed herein and that is selected from: (i) an unsaturated fatty acid; (ii) an unsaturated fatty alcohol; (iii) an esterification product of an unsaturated fatty acid with an alcohol; and (iv) an esterification product of a saturated fatty acid with an unsaturated alcohol. The olefinic substrate may also be a mixture of compounds.

Fatty acids are organic compounds comprising a hydrophobic carbon chain substituted with an acid moiety at one end. The hydrophobic portion is a carbon chain that typically contains at least six carbon atoms, and may contain up to 20 or more carbon atoms in the chain. The hydrophobic carbon chain may be substituted or unsubstituted, may contain one or more heteroatoms such as N, O, S or P, may contain one or more functional groups such as those described hereinabove, and may contain one or more unsaturated regions (e.g., carbon-carbon double bonds or triple bonds). The substituents on the hydrophobic carbon chain may be any of the substituents described hereinabove. The hydrophobic carbon chain contains an acid moiety at one end, and the acid moiety is typically a carboxylic acid. The carboxylic acid moiety may be ionized, such that it is in the form of a salt (e.g., a sodium or potassium salt). The carboxylic acid may also be derivitized using any of the derivitization methods typically employed for carboxylic acid compounds. For example, the carboxylic acid may be esterified via an esterification reaction with an alcohol. Any alcohol suitable for esterification with the fatty acid may be employed. The alcohol may be saturated or unsaturated, and may be monohydric, dihydric, or polyhydric. The alcohol may be a $C_1$-$C_{20}$ alcohol that optionally contains one or more heteroatoms, and optionally contains one or more substituents. The alcohol may optionally be cyclic and/or branched. Examples of alcohols suitable for preparing esters from the fatty acids disclosed herein include methanol, ethanol, propanol (e.g., isopropanol), butanol, 1,2-dihydroxypropane, and glycerol.

Fatty alcohols are organic compounds comprising a hydrophobic carbon chain substituted with an alcohol moiety (i.e., —OH) at one end. The hydrophobic carbon chain is as described for fatty acids hereinabove. As with fatty acids, the alcohol moiety may be ionized, such that it is in the form of a salt (e.g., a sodium or potassium salt). Also as with fatty acids, the alcohol may be derivatized using any derivatization methods employed for alcohols. For example, the alcohol may be converted to an ether via reaction with a compound containing another alcohol, or may be converted to an ester via reaction with a compound containing a carboxylic acid. Any alcohol or ester suitable for derivatizing the fatty alcohol may be employed. Such alcohols and esters include $C_1$-$C_{20}$ alcohol and esters that optionally contain one or more heteroatoms, and optionally contain one or more substituents. The alcohols and esters may optionally be cyclic and/or branched. Examples of alcohols and esters suitable for derivatizing the fatty alcohols disclosed herein include methanol and acetic acid.

The fatty acids and fatty alcohols suitable for use as the olefinic substrate in the methods disclosed herein are unsaturated fatty acids or fatty acid derivatives and unsaturated fatty alcohols or fatty alcohol derivatives. That is, the olefinic substrate comprises at least one unsaturated moiety. In one embodiment of the invention, the hydrophobic carbon chain of the fatty acid or fatty alcohol comprises at least one unsaturated moiety. In another embodiment of the invention, the olefinic substrate comprises a saturated fatty acid that is derivatized with an unsaturated compound, or the olefinic substrate comprises a saturated fatty alcohol that is derivitized with an unsaturated compound. For example, a saturated fatty acid may be esterified using an unsaturated alcohol.

Preferred unsaturated moieties are internal olefins. By "internal olefin" is meant an olefin wherein each of the olefinic carbons is substituted by at least one non-hydrogen substituent. The non-hydrogen substituents are selected from hydrocarbyl, substituted hydrocarbyl, heteroatom-containing hydrocarbyl, substituted heteroatom-containing hydrocarbyl, and functional groups. The internal olefin is therefore at least disubstituted, and may further include additional non-hydrogen substituents (e.g., a trisubstituted internal olefin). Each of the substituents on the internal olefinic carbons may be further substituted as described supra. The internal olefin may be in the Z- or E-configuration. When the olefinic substrate comprises a plurality of internal olefins, the olefinic substrate may comprise a mixture of internal olefins (varying in stereochemistry and/or substituent identity), or may comprise a plurality of identical internal olefins.

In general, the olefinic substrate may be represented by the formula $(R^I)(R^{II})C=C(R^{III})(R^{IV})$, wherein $R^I$, $R^{II}$, $R^{III}$, and $R^{IV}$ are independently selected from H, hydrocarbyl, substituted hydrocarbyl, heteroatom-containing hydrocarbyl, substituted heteroatom-containing hydrocarbyl, and functional groups, provided that at least one of $R^I$ or $R^{II}$ and at least one of $R^{III}$ or $R^{IV}$ is other than H. In a preferred embodiment, either $R^I$ or $R^{II}$ and either $R^{III}$ or $R^{IV}$ is H, such that the internal olefin is di-substituted.

In a preferred embodiment, the olefinic substrate is a derivative of glycerol, and has the structure of formula (I)

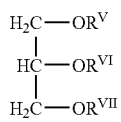

$$\begin{array}{c} H_2C-OR^V \\ | \\ HC-OR^{VI} \\ | \\ H_2C-OR^{VII} \end{array} \qquad (I)$$

wherein $R^V$, $R^{VI}$, and $R^{VII}$ are independently selected from hydrogen, hydrocarbyl, substituted hydrocarbyl, heteroatom-containing hydrocarbyl, substituted heteroatom-containing hydrocarbyl, and functional groups, provided that at least one of $R^V$, $R^{VI}$, and $R^{VII}$ is other than hydrogen and comprises an internal olefin.

As an example, the olefinic substrate is a "glyceride," and comprises glycerol esterified with 1, 2, or 3 fatty acids, such that the olefinic substrate is a monoacylglycerol, diacylglycerol, or triacylglycerol (i.e., a monoglyceride, diglyceride, or triglyceride, respectively). The olefinic substrate may also be a mixture of glycerides. Each fatty acid-derived fragment of the olefinic substrate may independently be saturated, monounsaturated, or polyunsaturated, and may furthermore derive (or be derivable) from naturally-occurring fatty acids or from synthetic fatty acids. Thus, the glyceride may be a compound with the structure of formula (I), wherein $R^V$, $R^{VI}$, or $R^{VII}$, or a combination thereof, is —C(=O)—$R^{VIII}$, wherein $R^{VIII}$, is hydrocarbyl, substituted hydrocarbyl, heteroatom-containing hydrocarbyl, or substituted heteroatom-containing hydrocarbyl, provided that at least one of $R^V$, $R^{VI}$, and $R^{VII}$ contains an unsaturated moiety. As a further example, the olefinic substrate may comprise glycerol esterified with one, two, or three fatty acids that are independently selected from palmitoleic acid, vaccenic acid, erucic acid, oleic acid, alpha-linolenic acid, gamma-linolenic acid, linoleic acid, gadoleic acid, arachidonic acid, docosahexaenoic acid (i.e., DHA), eicosapentaenoic acid (i.e., EPA), and $CH_3(CH_2)_n COOH$, where n is 2, 3, 4, 5, 6, 7, 8, 9, 10, 11, 12, 13, 14, 15, 16, 17, 18, 19, 20, 21, or 22.

The olefinic substrate may be solid (e.g., a fat) or liquid (e.g., an oil). Preferred glycerides that may be used as the olefinic substrate are seed oils and/or other vegetable oils, or are compounds that derive from seed oils and/or vegetable oils. Preferred oil sources include soybean oil, sunflower oil, canola oil, safflower oil, cottonseed oil, castor oil, rapeseed oil, peanut oil, corn oil, olive oil, palm oil, sesame oil, palm kernel oil, meadowfoam oil, grape seed oil, phospholipids, phosphoglycerides, phosphatidyl ethanolamine, phosphatidyl choline, ceramides, and sphingolipids. Further preferred oils include seed oil esters, such as jojoba oil and oils from animal sources such as fish oil, butterfat, lard, tallow, chicken fat, goose fat, menhaden oil, cod liver oil, herring oil, seal oil, shark oil, and whale oil.

The olefinic substrate may be a compound or mixture of compounds that is derived from a glyceride using any one or combination of methods well known in the chemical arts. Such methods include saponification, esterification, hydrogenation, isomerization, oxidation, and reduction. For example, the olefinic substrate may the carboxylic acid or mixture of carboxylic acids that result from the saponification of a monoacylglycerol, diacylglycerol, triacylglycerol, or mixture thereof. In a preferred embodiment, the olefinic substrate is a fatty acid methyl ester (FAME), i.e., the methyl ester of a carboxylic acid that is derived from a glyceride. Sunflower FAME, safflower FAME, soy FAME (i.e., methyl soyate), and canola FAME are examples of such olefinic substrates. Additionally, olefinic substrates may include derivatives of fatty acids such as oleamides, linoleamides, linolenamides, erucamide and substitution of the nitrogen with any combination of hydrogen, alkyl and aryl groups.

In addition, preferred olefinic substrates include seed oil-derived compounds such as methyl oleate.

Preferred fatty alcohol derivatives include oleyl chloride (ie 9-octadecenyl chloride), oleyl bromide, oleyl iodide, oleyl fluoride, linoleyl chloride (ie 9,12-octadecadienyl chloride), linoleyl bromide, linoleyl iodide, linoleyl fluoride, linolenyl chloride (ie 9,12,15-octadecatrienyl chloride), linolenyl bromide, linolenyl iodide, linolenyl fluoride, oleyl amine, linoleyl amine, linolenyl amine, oleyl thiol, linoleyl thiol, linolenyl thiol, oleyl phosphine, linoleyl phosphine, linolenyl phosphine.

In addition to the olefinic substrate, described hereinabove, the metathesis reactions disclosed herein involve a cross-metathesis partner. Preferred cross-metathesis partners include cyclic olefins, and any cyclic olefin suitable for the metathesis reactions disclosed herein may be used. Preferred cyclic olefins include optionally substituted, optionally heteroatom-containing, mono-unsaturated, di-unsaturated, or poly-unsaturated $C_5$ to $C_{24}$ hydrocarbons that may be mono-, di- or poly-cyclic. The cyclic olefin may be stained or unstrained.

Preferred cyclic olefins include $C_5$ to $C_{24}$ unsaturated hydrocarbons. Also preferred are $C_5$ to $C_{24}$ cyclic hydrocarbons that contain one or more (typically 2 to 12) heteroatoms such as O, N, S, or P. For example, crown ether cyclic olefins may include numerous 0 heteroatoms throughout the cycle, and these are within the scope of the invention. In addition, preferred cyclic olefins are $C_5$ to $C_{24}$ hydrocarbons that contain one or more (typically 2 or 3) olefins. For example, the cyclic olefin may be mono-, di-, or tri-unsaturated. Examples of cyclic olefins include cyclooctene, cyclododecene, and (c,t,t)-1,5,9-cyclododecatriene.

The cyclic olefins may also comprise multiple (typically 2 or 3) rings. For example, the cyclic olefin may be mono-, di-, or tri-cyclic. When the cyclic olefin comprises more than one ring, the rings may or may not be fused. Examples of cyclic olefins that comprise multiple rings include norbornene, dicyclopentadiene, and 5-ethylidene-2-norbornene.

The cyclic olefin may also be substituted—for example, a $C_5$ to $C_{24}$ cyclic hydrocarbon wherein one or more (typically 2, 3, 4, or 5) of the hydrogens are replaced with non-hydrogen substituents. Suitable non-hydrogen substituents may be chosen from the substituents described hereinabove. For example, functionalized cyclic olefins, i.e., $C_5$ to $C_{24}$ cyclic hydrocarbons wherein one or more (typically 2, 3, 4, or 5) of the hydrogens are replaced with functional groups, are within the scope of the invention. Suitable functional groups may be chosen from the functional groups described hereinabove. For example, a cyclic olefin functionalized with an alcohol group may be used to prepare a ring-insertion product comprising pendent alcohol groups. Functional groups on the cyclic olefin may be protected in cases where the functional group interferes with the metathesis catalyst, and any of the protecting groups commonly used in the art may be employed. Acceptable protecting groups may be found, for example, in Greene et al., *Protective Groups in Organic Synthesis*, 3$^{rd}$ Ed. (New York: Wiley, 1999). Examples of functionalized cyclic olefins include 2-hydroxymethyl-5-norbornene, 2-[(2-hydroxyethyl)carboxylate]-5-norbornene, Cydecanol, 5-n-hexyl-2-norbornene, 5-n-butyl-2-norbornene.

Cyclic olefins incorporating any combination of the above-mentioned features (i.e., heteroatoms, substituents, multiple olefins, multiple rings) are suitable for the methods disclosed herein.

The cyclic olefins useful in the methods disclosed herein may be strained or unstrained. It will be appreciated that the amount of ring strain varies for each compound, and depends upon a number of factors including the size of the ring, the presence and identity of substituents, and the presence of multiple rings. Ring strain is one factor in determining the reactivity of a molecule towards ring-opening olefin metathesis reactions. Highly strained cyclic olefins, such as certain bicyclic compounds, readily undergo ring opening reactions with olefin metathesis catalysts. Less strained cyclic olefins, such as certain unsubstituted hydrocarbon monocyclic olefins, are generally less reactive to such reactions. It should be noted, however, that in some cases, ring opening reactions of relatively unstrained (and therefore relatively unreactive) cyclic olefins becomes possible when performed in the presence of the olefinic substrates disclosed herein.

A plurality of cyclic olefins may be used as the cross-metathesis partner with the olefinic substrate. For example, two cyclic olefins selected from the cyclic olefins described hereinabove may be employed in order to form metathesis products that incorporate both cyclic olefins. Where two or more cyclic olefins are used, one example of a preferred second cyclic olefin is a cyclic alkenol, i.e., a $C_5$-$C_{24}$ cyclic hydrocarbon wherein at least one of the hydrogen substituents is replaced with an alcohol or protected alcohol moiety to yield a functionalized cyclic olefin.

The use of a plurality of cyclic olefins, and in particular when at least one of the cyclic olefins is functionalized, allows for further control over the positioning of functional groups within the products. For example, the density of cross-linking points can be controlled in polymers and macromonomers prepared using the methods disclosed herein. Control over the quantity and density of substituents and functional groups also allows for control over the physical properties (e.g., melting point, tensile strength, glass transition temperature, etc.) of the products. Control over these and other properties is possible for reactions using only a single cyclic olefin, but it will be appreciated that the use of a plurality of cyclic olefins further enhances the range of possible metathesis products.

A ring insertion reaction is carried out by contacting the at least one olefinic substrate with the cross metathesis partner, i.e., the at least one cyclic olefin, in the presence of the metathesis catalyst under reaction conditions effective to allow ring insertion cross metathesis whereby the cyclic olefin is simultaneously opened and inserted into the olefinic substrate. Examples are illustrated in Schemes 3, 4, and 5 in which an olefinic substrate is reacted with a cyclic olefin to produce metathesis products.

Scheme 3. Ring insertion cross metathesis using a single cyclic olefin.

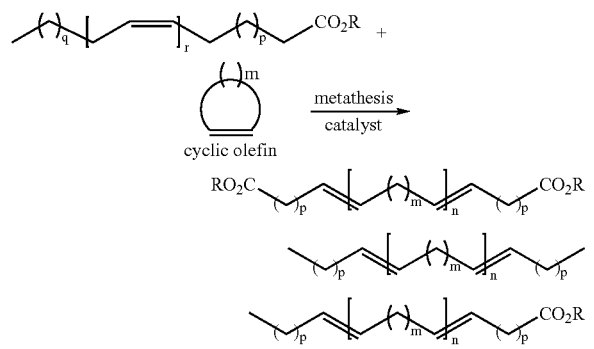

r = 0, 1, 2 or 3
m and n are any number
p and q are independently taken from 0 to 15
R = acyl glycerides and phospholipids
  Me for FAME and
  H for free acid Scheme 4. Ring insertion cross metathesis using a single cyclic olefin.

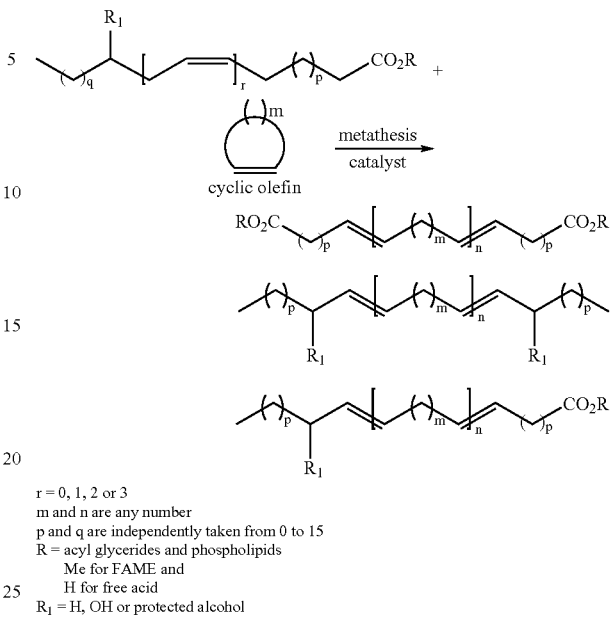

r = 0, 1, 2 or 3
m and n are any number
p and q are independently taken from 0 to 15
R = acyl glycerides and phospholipids
  Me for FAME and
  H for free acid
$R_1$ = H, OH or protected alcohol In Scheme 3 and Scheme 4, the ring insertion cross metathesis reactions are carried out using seed oils as the olefinic substrates to produce chain extended trialkylglycerides (TAGs) and chain extended fatty acid methyl esters (FAMEs). The metathesis products shall, however, not be limited to these specific products and can include any mixtures of chain extended fatty acid components, mixtures of chain extended olefin components, and mixtures of chain extended diacid components.

An illustration of a ring opening cross metathesis reaction in which a cycloalkene and a cyclic alkenol are employed is provided in Scheme 5. The product from the reaction shown in scheme 5 is a copolymer that contains pendent alcohol groups dispersed throughout the backbone. It will be appreciated that the spacing between alcohol groups along the product polymer backbone will be dependent upon the relative amounts of cyclic olefin and cyclic alkenol that are incorporated into the polymer. Therefore, relative amounts of cyclic olefin and cyclic alkenol added to the reaction mixture is one way in which this spacing can be controlled.

Scheme 5. Ring insertion cross metathesis using a plurality of cyclic olefins.

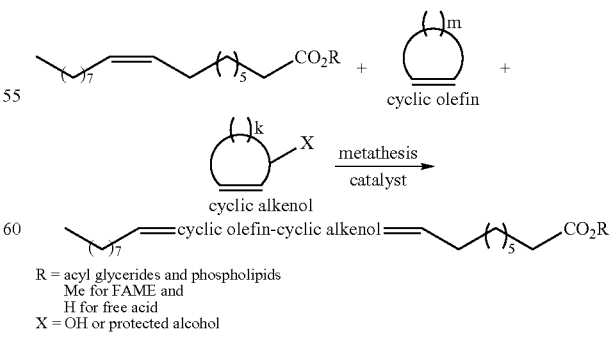

R = acyl glycerides and phospholipids
  Me for FAME and
  H for free acid
X = OH or protected alcohol The reactions disclosed herein are catalyzed by any of the metathesis catalysts that are described infra. The catalyst is typically added to the reaction medium as a solid, but may also be added as a solution wherein the catalyst is dissolved in an appropriate solvent, or as a suspension wherein the catalyst is suspended in an appropriate liquid. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of the olefinic substrate. Catalyst loading, when measured in ppm relative to the amount of the olefinic substrate, is calculated using the equation $$ppm \text{ catalyst} = \frac{\text{moles catalyst}}{\text{moles olefinic substrate}} * 1{,}000{,}000.$$

Alternatively, the amount of catalyst can be measured in terms of mol % relative to the amount of olefinic substrate, using the equation $$\text{mol \% catalyst} = \frac{\text{moles catalyst}}{\text{moles olefinic substrate}} * 100.$$

Thus, the catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

In a preferred embodiment, the reactions disclosed herein are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions disclosed herein may also be carried out in an oxygen-containing and/or a water-containing atmosphere, and in one embodiment, the reactions are carried out under ambient conditions. The presence of oxygen or water in the reaction may, however, necessitate the use of higher catalyst loadings as compared with reactions performed under an inert atmosphere.

Where the vapor pressure of the reactants allows, the reactions disclosed herein may also be carried out under reduced pressure.

The olefin metathesis catalyst for carrying out the reactions disclosed herein is preferably a Group 8 transition metal complex having the structure of formula (II)

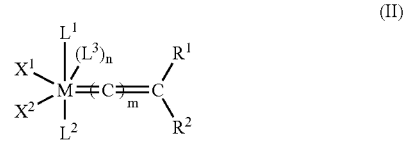

(II)

in which the various substituents are as follows.
  M is a Group 8 transition metal;
  $L^1$, $L^2$ and $L^3$ are neutral electron donor ligands;
  n is 0 or 1, such that $L^3$ may or may not be present;

m is 0, 1, or 2;
  $X^1$ and $X^2$ are anionic ligands; and
  $R^1$ and $R^2$ are independently selected from hydrogen, hydrocarbyl, substituted hydrocarbyl, heteroatom-containing hydrocarbyl, substituted heteroatom-containing hydrocarbyl, and functional groups,
  wherein any two or more of $X^1$, $X^2$, $L^1$, $L^2$, $L^3$, $R^1$, and $R^2$ can be taken together to form one or more cyclic groups, and further wherein any one or more of $X^1$, $X^2$, $L^1$, $L^2$, $L^3$, $R^1$, and $R^2$ may be attached to a support.

Preferred catalysts contain Ru or Os as the Group 8 transition metal, with Ru particularly preferred.

Numerous embodiments of the catalysts useful in the reactions disclosed herein are described in more detail infra. For the sake of convenience, the catalysts are described in groups, but it should be emphasized that these groups are not meant to be limiting in any way. That is, any of the catalysts useful in the invention may fit the description of more than one of the groups described herein.

A first group of catalysts, then, are commonly referred to as First Generation Grubbs-type catalysts, and have the structure of formula (II). For the first group of catalysts, M and m are as described above, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —C=C(CH$_3$)$_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as Second Generation Grubbs-type catalysts, have the structure of formula (II), wherein $L^1$ is a carbene ligand having the structure of formula (III)

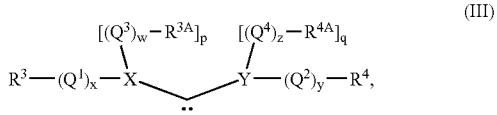

such that the complex may have the structure of formula (IV)

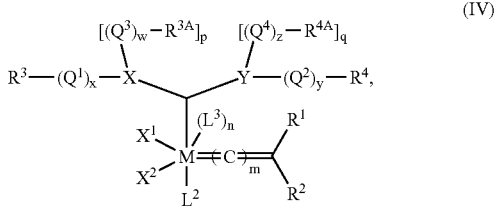

wherein M, m, n, $X^1$, $X^2$, $L^2$, $L^3$, $R^1$, and $R^2$ are as defined for the first group of catalysts, and the remaining substituents are as follows.

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

Preferably, $R^{3A}$ and $R^{4A}$ are linked to form a cyclic group so that the carbene ligand has the structure of formula (V)

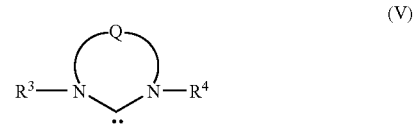

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands suitable as $L^1$ thus include, but are not limited to, the following:

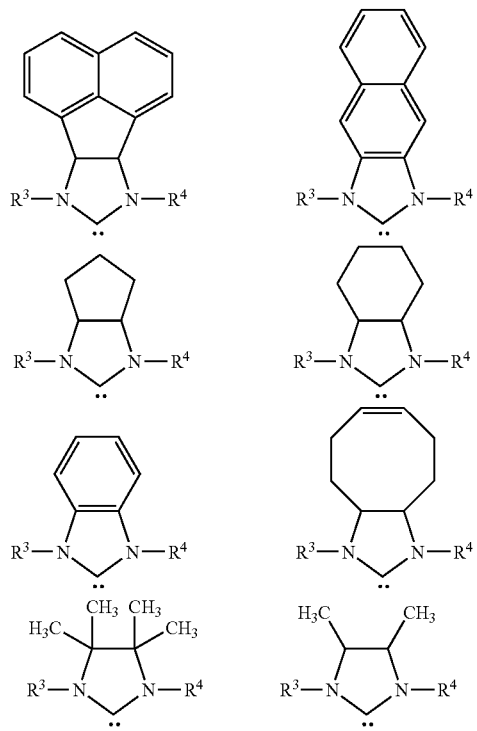

-continued

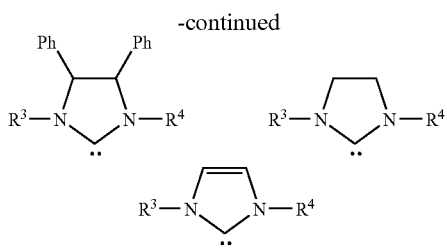

When M is ruthenium, then, the preferred complexes have the structure of formula (VI)

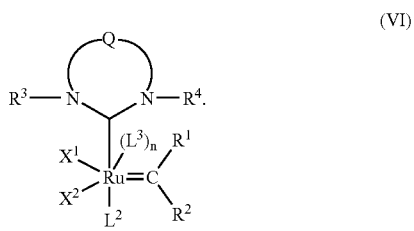

(VI)

In a more preferred embodiment, Q is a two-atom linkage having the structure $-CR^{11}R^{12}-CR^{13}R^{14}-$ or $-CR^{11}=CR^{13}-$, preferably $-CR^{11}R^{12}-CR^{13}R^{14}-$, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl.

In a third group of catalysts having the structure of formula (II), M, m, n, $X^1$, $X^2$, $R^1$, and $R^2$ are as defined for the first group of catalysts, $L^1$ is a strongly coordinating neutral electron donor ligand such as any of those described for the first and second group of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on L and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VII)

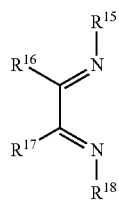

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (I), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein $L^2$ and $R^2$ are linked are examples of the fourth group of catalysts, and are commonly called "Grubbs-Hoveyda" catalysts. Examples of Grubbs-Hoveyda-type catalysts include the following:

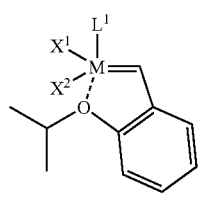 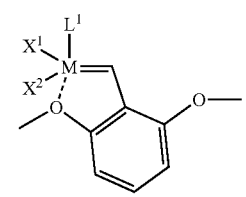

-continued

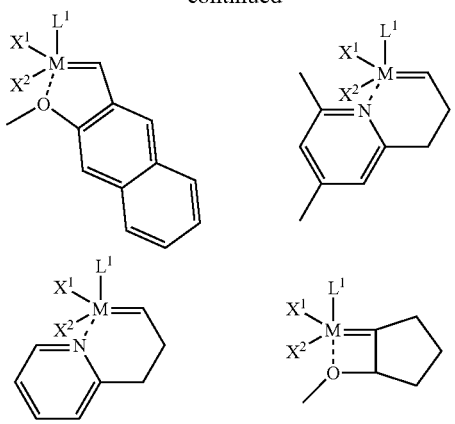

wherein $L^1$, $X^1$, $X^2$, and M are as described for any of the other groups of catalysts.

In addition to the catalysts that have the structure of formula (II), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (VIII);

neutral ruthenium or osmium metal carbene complexes containing metal centers that are formally in the +2 oxidation state, have an electron count of 18, are hexa-coordinated, and are of the general formula (IX);

cationic ruthenium or osmium metal carbene complexes containing metal centers that are formally in the +2 oxidation state, have an electron count of 14, are tetra-coordinated, and are of the general formula (X); and cationic ruthenium or osmium metal carbene complexes containing metal centers that are formally in the +2 oxidation state, have an electron count of 14, are penta-coordinated, and are of the general formula (XI)

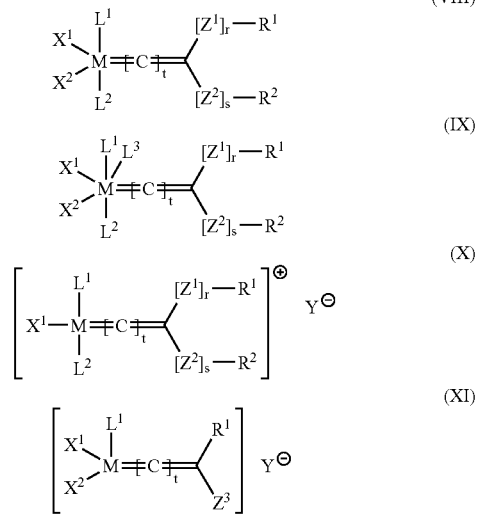

wherein: $X^1$, $X^2$, $L^1$, $L^2$, n, $L^1$, $R^1$, and $R^2$ are as defined for any of the previously defined four groups of catalysts; r and s are independently zero or 1; t is an integer in the range of zero to 5; Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P($R^2$)$_3^+$ or —N($R^2$)$_3^+$; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support.

As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

Non-limiting examples of catalysts that may be used in the reactions disclosed herein include the following, some of which for convenience are identified throughout this disclosure by reference to their molecular weight:

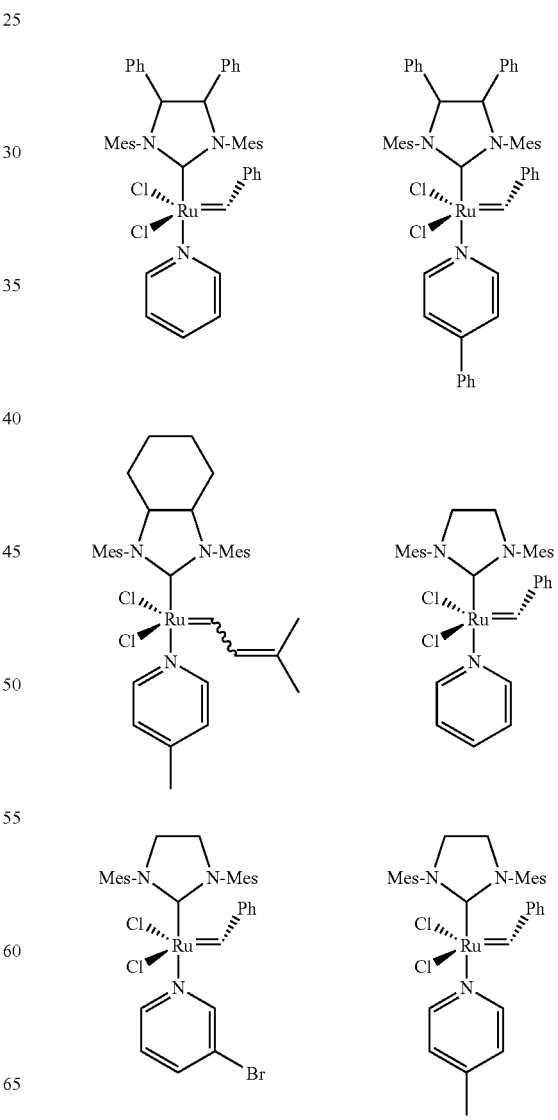

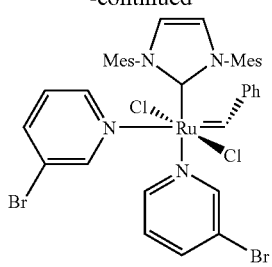
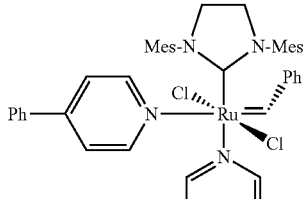
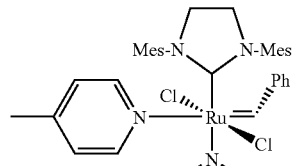
C884
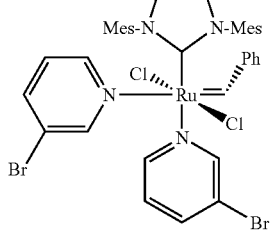
C727
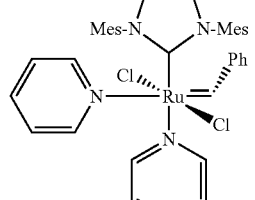
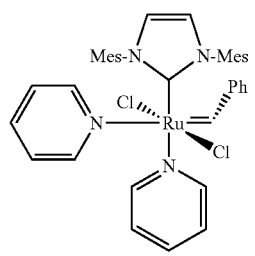
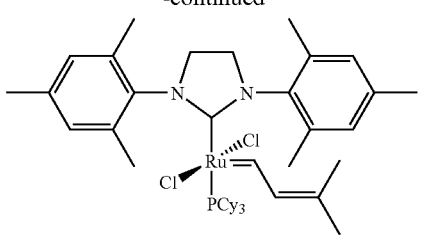
C827
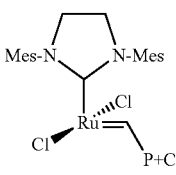
C859
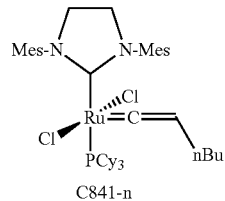
C841-n
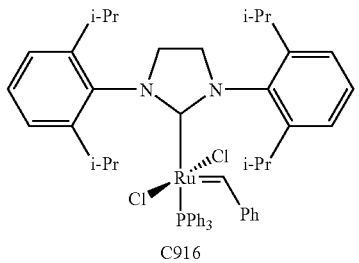
C916
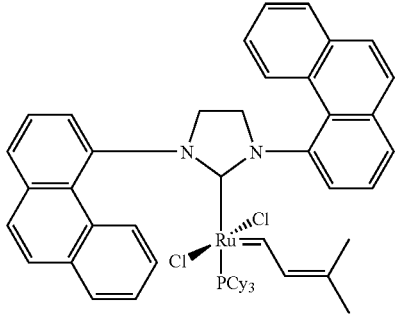
C965-p
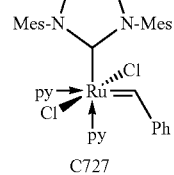
C727
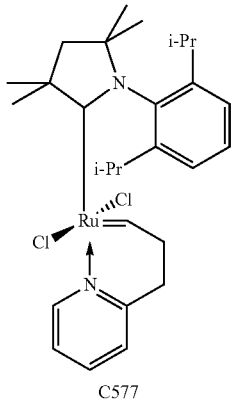
C577

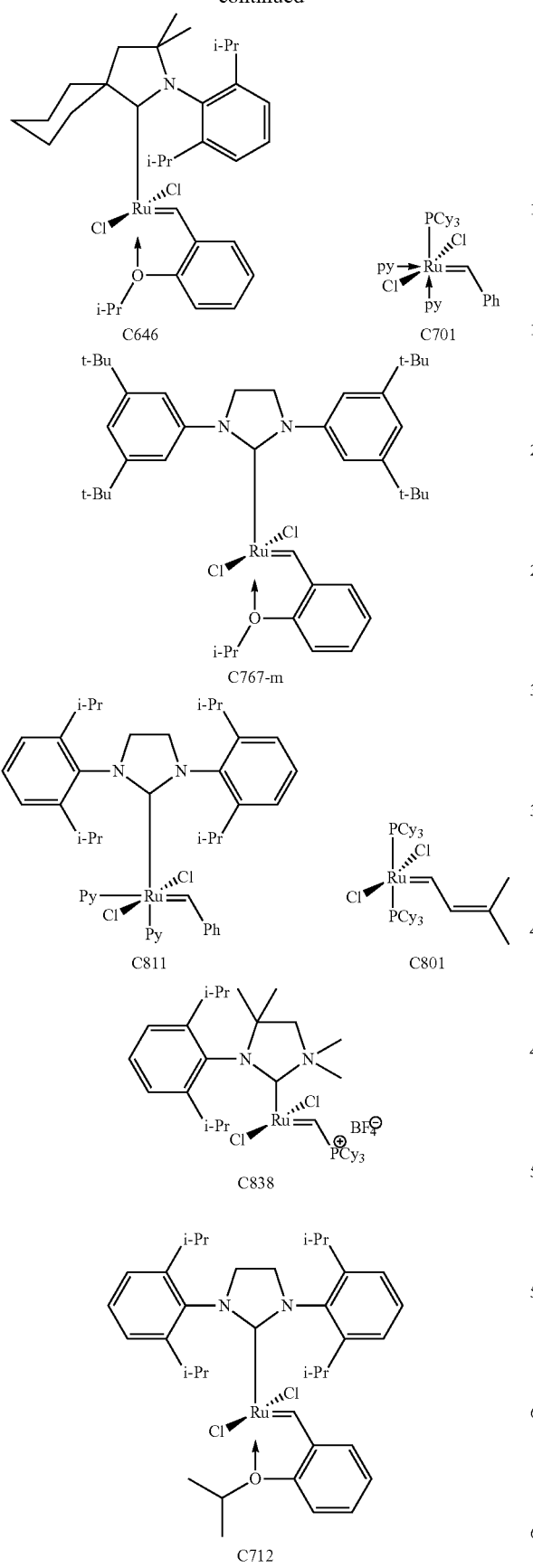
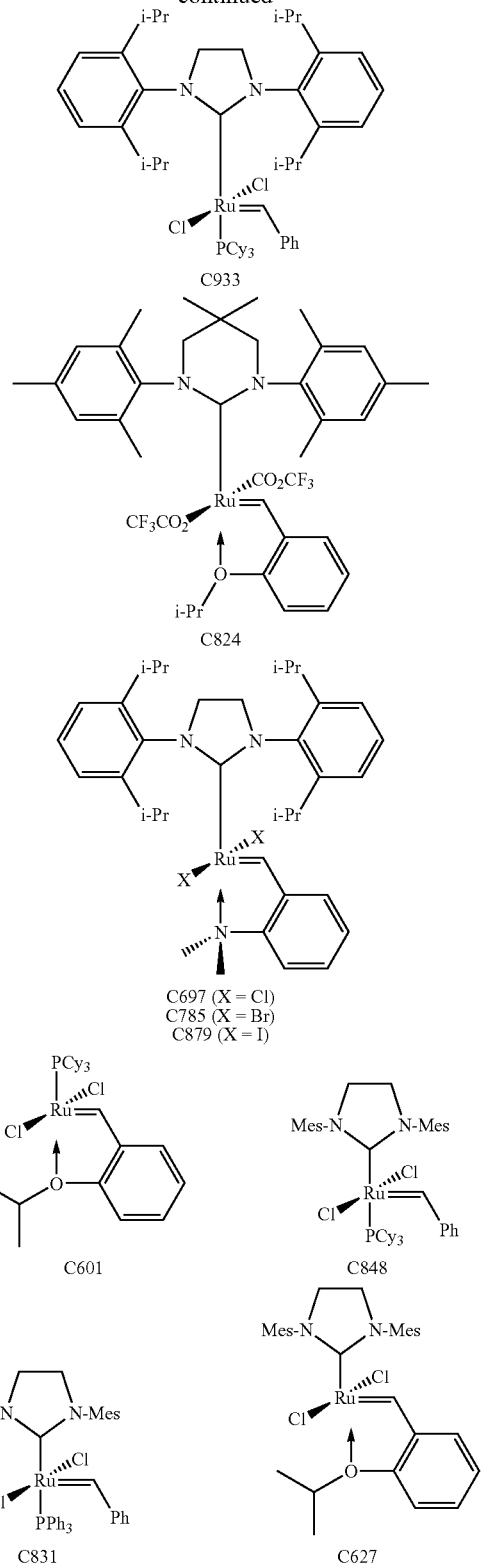
In the foregoing molecular structures and formulae, Ph represents phenyl, Cy represents cyclohexyl, Me represents methyl, nBu represents n-butyl, i-Pr represents isopropyl, py represents pyridine (coordinated through the N atom), and Mes represents mesityl (i.e., 2,4,6-trimethylphenyl).

Further examples of catalysts useful in the reactions disclosed herein include the following: ruthenium (II) dichloro (3-methyl-1,2-butenylidene) bis(tricyclopentylphosphine) (C716); ruthenium (II) dichloro(3-methyl-1,2-butenylidene) bis(tricyclohexylphosphine) (C801); ruthenium (II) dichloro (phenylmethylene) bis(tricyclohexylphosphine) (C823); ruthenium (II) [1,3-bis-(2,4,6-trimethylphenyl)-2-imidazolidinylidene) dichloro (phenylmethylene) (triphenylphosphine) (C830), and ruthenium (II) dichloro(vinyl phenylmethylene) bis(tricyclohexylphosphine) (C835); ruthenium (II) dichloro (tricyclohexylphosphine) (o-isopropoxyphenylmethylene) (C601), and ruthenium (II) (1,3-bis-(2,4,6,-trimethylphenyl)-2-imidazolidinylidene) dichloro(phenylmethylene) (bis 3-bromopyridine (C884)).

Still further catalysts useful in the ring-opening cross-methathesis (ROCM) reactions disclosed herein include the following, identified as structures 60-68:

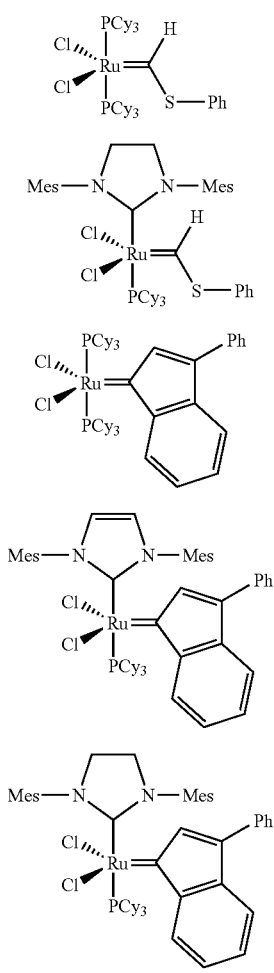

The transition metal complexes used as catalysts herein can be prepared by several different methods, such as those described by Schwab et al. (1996) *J. Am. Chem. Soc.* 118: 100-110, Scholl et al. (1999) *Org. Lett.* 6:953-956, Sanford et al. (2001) *J. Am. Chem. Soc.* 123:749-750, U.S. Pat. No. 5,312,940 and U.S. Pat. No. 5,342,909. Also see U.S. Patent Publication No. 2003/0055262 to Grubbs et al. filed Apr. 16, 2002 for "Group 8 Transition Metal Carbene Complexes as Enantioselective Olefin Metathesis Catalysts", International Patent Publication No. WO 02/079208 application Ser. No. 10/115,581 to Grubbs, Morgan, Benitez, and Louie, filed Apr. 2, 2002, for "One-Pot Synthesis of Group 8 Transition Metal Carbene Complexes Useful as Olefin Metathesis Catalysts," commonly assigned herewith to the California Institute of Technology. Preferred synthetic methods are described in International Patent Publication No. WO 03/11455A1 to Grubbs et al. for "Hexacoordinated Ruthenium or Osmium Metal Carbene Metathesis Catalysts," published Feb. 13, 2003.

The components of the reactions disclosed herein may be combined in any order, and it will be appreciated that the order of combining the reactants may be adjusted as needed. For example, the olefinic substrate may be added to the cross-metathesis partner, followed by addition of the catalyst. Alternatively, the olefinic substrate and cross-metathesis partner may be added to the catalyst. When one of the reactants is a gas, it may be necessary to add the catalyst to the liquid or solid reactant before introducing the gaseous reactant.

The catalyst may be added to the reaction either as a solid, dissolved in one of the reactants, or dissolved in a solvent.

The reactions disclosed herein may be carried out in a solvent, and any solvent that is inert towards cross-metathesis may be employed. Generally, solvents that may be used in the cross-metathesis reactions include organic, protic, or aqueous solvents, such as aromatic hydrocarbons, chlorinated hydrocarbons, ethers, aliphatic hydrocarbons, alcohols, water, or mixtures thereof. Example solvents include benzene, toluene, p-xylene, methylene chloride, 1,2-dichloroethane, dichlorobenzene, chlorobenzene, tetrahydrofuran, diethylether, pentane, methanol, ethanol, water, or mixtures thereof. In a preferred embodiment, the reactions disclosed herein are carried out neat, i.e., without the use of a solvent.

It will be appreciated that the temperature at which a cross-metathesis reaction according to methods disclosed herein is conducted can be adjusted as needed, and may be at least about −78° C., −40° C., −10° C., 0° C., 10° C., 20° C., 25° C., 35° C., 50° C., 70° C., 100° C., or 150° C., or the temperature may be in a range that has any of these values as the upper or lower bounds. In a preferred embodiment, the reactions are carried out at a temperature of at least about 35° C., and in another preferred embodiment, the reactions are carried out at a temperature of at least about 50° C.

It will further be appreciated that the molar ratio of the reactants will be dependent upon the identities of the reactants and the desired products. Although the cyclic olefin and the olefinic substrate may be used in equal molar amounts, in general, an excess of cyclic olefin with respect to the olefinic substrate will be present. For example, the molar ratio of the cyclic olefin (as the sum of all compounds when the cyclic olefin comprises a plurality of cyclic compounds) to the olefinic substrate may be up to 2:1, 5:1, 10:1, 25:1, 50:1, 100:1, 250:1, 500:1, 1000:1, 5000:1, 10,000:1, 50,000:1, or 100,000:1, or within a range that has any of these values as the upper or lower bounds.

When the cyclic olefin comprises a cyclic olefinic hydrocarbon and a cyclic alkenol, the molar ratio of the two compounds will vary depending on the desired products. For example, the molar ratio of the cyclic olefinic hydrocarbon to the cyclic alkenol may be 100:1, 50:1, 25:1, 10:1, 5:1, 2:1, 1:1, 1:2, 1:5, 1:10, 1:25, 1:50, or 1:100, or within a range that has any of these values as the upper or lower bounds.

II. Second Embodiment

Further Reactions

In a second embodiment, the invention provides a method for manufacturing a wax. The method involves ring-opening, ring insertion metathesis of at least one olefinic substrate and at least one cyclic olefin as the cross metathesis partner. As with the first embodiment, the olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol. The reaction is carried out catalytically, generally in the presence of a ruthenium alkylidene metathesis catalyst, by contacting the at least one olefinic substrate with the cross metathesis partner, i.e., the at least one cyclic olefin, in the presence of the metathesis catalyst under reaction conditions effective to allow ring insertion cross metathesis whereby the cyclic olefin is simultaneously opened and inserted into the olefinic substrate to provide an olefinic product. This embodiment further comprises partially or completely hydrogenating the olefinic product. The disclosure, supra, with respect to the components and methods of the first embodiment also applies to the second embodiment.

Methods suitable for carrying out the partial or complete hydrogenation of the olefinic product are known in the art, and any appropriate hydrogenation method may be employed. Typically, such methods involve placing the olefinic product in a suitable container, introducing a hydrogenation catalyst, if necessary, and introducing a hydrogen source. Suitable methods for hydrogenation may be found, for example, in Smith et al. *March's Advanced Organic Chemistry, 5th Edition* (Wiley: New York, 2001).

The hydrogenation of the olefinic product of the reaction may be carried out with or without isolation of the olefinic products from the ring insertion cross metathesis reaction. It will be appreciated that the hydrogenation reaction will, in some instances, be affected by the purity of the reaction mixture and the presence of impurities from the ring insertion cross metathesis reaction. In such cases, the yield of the hydrogenated olefinic products can be maximized by isolating and purifying the olefinic products before hydrogenation is performed.

Any catalyst suitable for hydrogenating the olefinic products may be employed, and appropriate catalysts may also be found, for example, in Smith et al. *March's Advanced Organic Chemistry, 5th Edition* (Wiley: New York, 2001). In one example, the ruthenium alkylidene metathesis catalysts that is used for the ring insertion cross metathesis reaction may also be employed as the hydrogenation catalyst. In this embodiment, it is not necessary to add a further hydrogenation catalyst to the reaction mixture in order to perform the hydrogenation.

III. Third Embodiment

Process with the Grubbs-Hoveyda Catalyst

In a third embodiment, the invention provides an olefin cross-metathesis method in which the method involves ring-opening, ring insertion metathesis of at least one olefinic substrate and at least one cyclic olefin as the cross metathesis partner. The reaction is carried out catalytically, generally in the presence of a ruthenium alkylidene metathesis catalyst. In this embodiment, the reaction is carried out by contacting the at least one olefinic substrate with the cross metathesis partner, i.e., the at least one cyclic olefin, in the presence of the metathesis catalyst under reaction conditions effective to allow ring insertion cross metathesis whereby the cyclic olefin is simultaneously opened and inserted into the olefinic substrate. Furthermore, in this embodiment, the catalyst is a Grubbs-Hoveyda complex, as described in detail for the first embodiment, supra.

IV. Fourth Embodiment

Reaction System

In a fourth embodiment, the invention provides a reaction system. As an example, a reaction system is provided for carrying out a catalytic ring-opening cross-metathesis reaction comprising at least one olefinic substrate, at least one cyclic olefin, and a ruthenium alkylidene olefin metathesis catalyst. The at least one olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol. The reaction system may further comprise a solvent.

In a second example of this embodiment, the reaction mixture comprises at least one olefinic substrate, an unsubstituted cyclic olefin, a cyclic alkenol, and a ruthenium alkylidene metathesis catalyst.

In another example, a reaction system is provided for manufacturing a wax. The reaction system comprises at least one olefinic substrate, at least one cyclic olefin, and a ruthenium alkylidene olefin metathesis catalyst. The at least one olefinic substrate is selected from: (i) an unsaturated fatty acid; (ii) an unsaturated fatty alcohol; (iii) an esterification product of an unsaturated fatty acid with an alcohol; and (iv) an esterification product of a saturated fatty acid with an unsaturated alcohol.

Detailed descriptions of each of these reaction components can be found in the disclosure of the first embodiment, supra.

V. Fifth Embodiment

Products

In a fifth embodiment, the invention provides compounds and compositions. For example, the invention provides compounds that are prepared using any of the reactions and/or reaction systems disclosed herein. Such compounds may be monomers, dimmers, trimers, oligomers, higher order species, or mixtures thereof. Such compounds may be chain-extended olefinic substrates such as glycerides. Examples of chain-extended glycerides include chain-extended monoglycerides, chain-extended diglycerides, chain-extended triglycerides, higher order chain-extended glycerides, and combinations thereof.

VI. Sixth Embodiment

Kit of Parts

In a fifth embodiment, the invention provides a kit of parts. As an example, a kit of parts is provided for carrying out a catalytic ring-opening cross metathesis reaction. The kit of parts comprises at least one olefinic substrate and a ruthenium alkylidene olefin metathesis catalyst. The catalyst is present in an amount that is less than 1000 ppm relative to the olefinic substrate, and the at least one olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol. The kit of parts further comprises: (a) at least one cyclic olefin; or (b)

instructions for adding a cyclic olefin to the at least one olefinic substrate. The at least one olefinic substrate, the ruthenium alkylidene olefin metathesis catalyst, and the at least one cyclic olefin (when present) may be combined in a mixture or may be contained separately.

In a preferred embodiment of the kit of parts for carrying out a catalytic ring-opening cross metathesis reaction, the kit comprises at least one cyclic olefin. The at least one olefinic substrate is combined in a mixture with the at least one olefinic substrate, and this mixture is contained separately from the ruthenium alkylidene olefin metathesis catalyst.

In another example, a kit of parts is provided for manufacturing a wax. The kit of parts comprises at least one olefinic substrate and a ruthenium alkylidene olefin metathesis catalyst. The catalyst is present in an amount that is less than 1000 ppm relative to the olefinic substrate, and the at least one olefinic substrate is selected from (i) an unsaturated fatty acid, (ii) an unsaturated fatty alcohol, (iii) an esterification product of an unsaturated fatty acid with an alcohol, and (iv) an esterification product of a saturated fatty acid with an unsaturated alcohol. The kit of parts further comprises: (a) at least one cyclic olefin; or (b) instructions for adding a cyclic olefin to the at least one olefinic substrate. The kit of parts further comprises instructions for hydrogenating metathesis products, and the kit may further comprises materials useful for hydrogenating metathesis products.

In a preferred embodiment of the kit of parts for manufacturing a wax, the kit comprises at least one cyclic olefin. The at least one olefinic substrate is combined in a mixture with the at least one olefinic substrate, and this mixture is contained separately from the ruthenium alkylidene olefin metathesis catalyst.

Detailed descriptions of each of these reaction components can be found in the disclosure of the first embodiment, supra.

Utility

The metathesis products from the methods disclosed herein are useful, for example, as binders in urethane foams, latex paints, printing inks and as high melting point waxes. As described hereinabove, the double bonds may be partially or completely hydrogenated to produce waxes of varying melting points.

It is to be understood that while the invention has been described in conjunction with specific embodiments thereof, that the description above as well as the examples that follow are intended to illustrate and not limit the scope of the invention. Other aspects, advantages, and modifications within the scope of the invention will be apparent to those skilled in the art to which the invention pertains.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

EXAMPLES

General Metathesis Procedure for Production and Analysis of Metathesized Oil Polyol and Chain-Extended Samples. To a clean and dry 2-L round-bottomed flask is added approximately 500 g of seed oil (e.g., refined bleached deodorized soybean oil (RBDSBO), Castor Oil, volatile lights removed metathesized soybean oil (RMSBO), soybean oil fatty acid methyl esters (Soy FAME), caster oil fatty acid methyl esters (Castor FAME), etc.) containing a PTFE lined stir bar. To the oil is added one or more reagents (e.g., cyclooctene, 5-hydroxymethyl-2-norbornene, etc.), in mole ratio ranging from 0.1 mol % to 200 mol %. The mixture is degassed with Argon for one hour with stirring. After degassing, an appropriate mass of metathesis catalyst such as C827 (1) (i.e., [1,3-bis(2,4,6-trimethylphenyl)-2-imidazolidinylidene]dichloro[3-methyl-2-buteneylidene]-tricyclohexylphosphine) ruthenium) is added as a solid to the reaction mixture at room temperature, at which point the vessel is blanketed with Argon, sealed, and placed in a 70° C. oil bath. When the temperature of the bath reaches 70° C. again, the time is recorded and the reaction is allowed to stir for two hours. The catalyst may be removed or the reaction mixture can be used without further purification. After two hours, an aliquot is taken from the reaction and added to about 1 mL of 1% NaOMe/MeOH solution in a vial, which is placed in a heating block at 70° C. for 30 min in order to transesterify the triglyceride products into methyl esters. After 30 min, the solution is allowed to cool. The cooled solution is hydrolyzed, and then the organics extracted using a relatively non-polar solvent (e.g., hexanes, ether, etc.). The organic layer is analyzed by GC; unless otherwise noted, conversion is calculated and reported based on the disappearance of the starting material. It is noted whether all or some of the reaction solidified, and, in some cases, a viscosity measurement is taken.

Catalyst Removal Procedure: A 1.0 M solution of tris(hydroxymethyl)phosphine (THMP) in isopropanol (IPA) (25 mol equiv of THMP per mole of metathesis catalyst) was added to the metathesized oil and the mixture was heated at 70° C. for 6 hours (under argon) (R. L. Pederson; I. M. Fellows; T. A. Ung; H. Ishihara; S. P Hajela *Adv. Syn. Cat.* 2002, 344, 728). Hexanes was added if needed to form a second phase when the mixture was washed 3 times with water. The organic phase was dried with anhydrous $Na_2SO_4$, filtered and analyzed by GC analysis.

Alternative Catalyst Removal Procedure: A 1.0 M solution of tris(hydroxymethyl)phosphine (THMP) in IPA (25 mol equiv of THMP per mole of metathesis catalyst) was added to the metathesized oil and the mixture was heated at 70° C. for 6 hours (under argon) (R. L. Pederson; I. M. Fellows; T. A. Ung; H. Ishihara; S. P Hajela *Adv. Syn. Cat.* 2002, 344, 728). IPA was then removed via rotary evaporator (part of volatile terminal olefins were also removed), 5 wt % of bleaching clay (Pure Flow B80 CG) to product was added to the crude reaction mixture and stirred overnight under argon at 70° C. The crude product mixture containing the clay was subsequently filtered through a packed bed of sand (10 g), celite (5 g), bleaching clay (12.5 g), and sand (10 g). The filtered oil was analyzed by GC analysis.

General Procedure for the Transesterification of Metathesized Seed oils: To a glass 3-necked round bottom flask with a magnetic stirrer, condenser, temperature probe, and a gas adapter was charged with crude metathesized SBO product (~1 L) and 1% w/w NaOMe in MeOH (~3 L). The resulting light yellow heterogeneous mixture was stirred at 60° C. for 1 hr. Towards the end of the hour, the mixture turned a homogeneous orange color. Esterified products were transferred into the separatory funnel and extracted with 2.0 L DI—$H_2O$. The aqueous layer was then extracted with 2×2.0 L $Et_2O$. The combined organic extracts were dried over 300 g. of anhydrous $Na_2SO_4$ for 20 hours. The solution of esterified products was filtered and the filtrate was stripped of solvent via rotary evaporator.

Viscosity methods: All readings were taken at 30° C. using a Brookfield Digital Viscometer Model DV-II and S62 spindle. RPM values were dependent on individual viscosity of the material.

GC Analysis Conditions and methods: The products were analyzed using an Agilent 6890 gas chromatography (GC) instrument with a flame ionization detector (FID). The following conditions and equipment were used:

| Column: | Rtx-5, 30 m × 0.25 mm (ID) × 0.25 µm film thickness. |
|---|---|
| Manufacturer: | Restek |
| GC and column conditions: | Injector temperature: 250° C. |
| | Detector temperature: 280° C. |
| Oven temperature: | Starting temperature: 100° C., hold time: 1 minute. |
| | Ramp rate 10° C./min to 250° C., hold time: 12 minutes. |
| | Carrier gas: Helium |
| Mean gas velocity: | 31.3 ± 3.5% cm/sec (calculated) |
| Split ratio: | ~50:1 |

The products were characterized by comparing peaks with known standards, in conjunction with supporting data from mass spectrum analysis (GCMS-Agilent 5973N). GCMS analysis was accomplished with a second Rtx-5, 30 m×0.25 mm (ID)×0.25 µm film thickness GC column, using the same method as above.

Materials and methods: Seed oils were obtained from Cargill. In the Examples that follow, all reactions were carried out using the specified catalyst loading as moles of catalyst to moles of seed oils. Catalysts are referenced using their molecular weights, as described hereinabove. In the Examples, the abbreviation RMSBO refers to Removed-Lights Metathesized Soy Bean Oil, which is self-metathesized RBSBO in which the light oils and olefins have been removed by flash distillation. Self-metathesis of seed oils is described in WO 2006/076364. Reference is also made to various cyclic olefins using the following abbreviations:

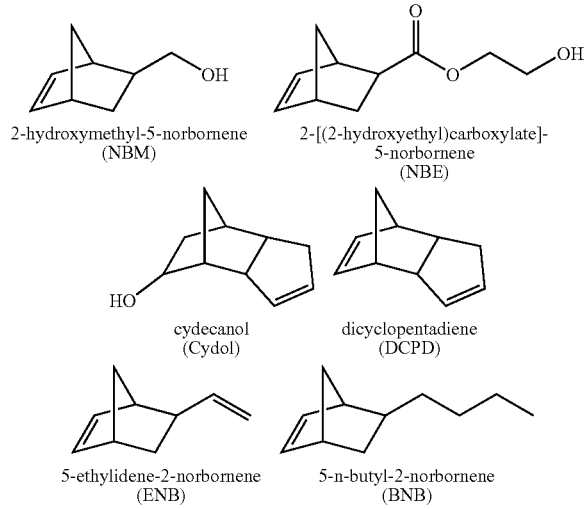

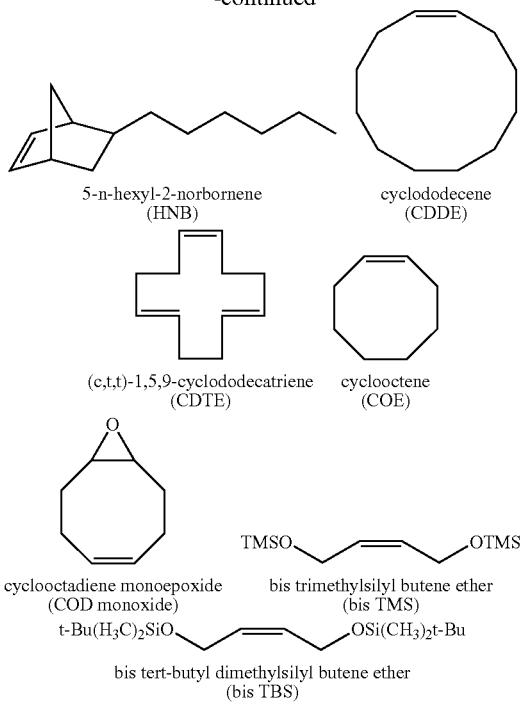

Example 1

Various compounds were analyzed using the GCMS methods described above. Data are provided in table 1.

TABLE 1

Common Products from the Cross Metathesis of Seed Oils.

| Ret Time (min) | Compound | Compound Abbreviation |
|---|---|---|
| 1.300 | E-2-Octene | $2C_8$ |
| 1.596 | 3-Nonene | $3C_9$ |
| 2.039 | 1-Decene | $1C_{10}$ |
| 2.907 | E-2-Undecene | $E\text{-}2C_{11}$ |
| 3.001 | Z-2-Undecene | $Z\text{-}2C_{11}$ |
| 3.836 | 3-Dodecenes | $3C_{12}$ |
| 5.298 | Methyl 9-Decenoate | $9C_{10}O_2Me$ |
| 7.419 | Pentadecadienes | $nC_{15}$ |
| 7.816 | Methyl E-9-Dodecenoate | $E\text{-}9C_{12}O_2Me$ |
| 7.894 | Methyl Z-9-Dodecenoate | $Z\text{-}9C_{12}O_2Me$ |
| 10.939 | 9-Octadecene | $9C_{18}$ |
| 11.290 | Methyl 9-12 tetradecadienoate | $9,12C_{14}O_2Me$ |
| 12.523 | Methyl palmitate | $C_{16}O_2Me$ |
| 14.306 | Methyl linoleates | $9,12C_{18}O_2Me$ |
| 14.363 | Methyl oleates | $9C_{18}O_2Me$ |
| 14.537 | Methyl stearate | $C_{18}O_2Me$ |
| 17.138 | Methyl 9,21-Henicosadienaote | $9,12C_{18}O_2Me$ |
| 17.586 | 1,18 Dimethyl ester of 9-Ocadecene | $9,12C_{18}O_2Me$ |
| 22.236 | Methyl 9,12,15-docosatrienoate | $9,12,15C_{21}O_2Me$ |

Example 2

A model study was undertaken to prove that ROCM reactions produced the desired higher molecular weight products. This study examined reaction of simple acyclic olefins with cyclooctene to determine and characterize the ROCM products formed.

In a ROCM reaction, a cyclic alkene undergoes the ring-opening metathesis reaction to produce the mixture of ring-opened products. Once opened, it will cross metathesize with an acyclic alkene such as SBO or SBO FAME to yield a new high molecular weight product. Hence the ROCM product should be a mixture of cyclic alkene inserted-products. To understand the ROCM product distributions, several ROCM reactions have been studied under different ratios of cyclic alkene to acyclic alkene.

GC and GC-MS Results of ROCM Products:

Conversion in each reaction was determined by measuring the disappearance of the starting internal alkene when compared to dodecane as an internal standard. The GC and GC-MS analyses were determined and ROCM products were characterized up to n=3 cyclic olefin inserted products. When n was >3, these products were above our detection limit of our instruments. The ratio of higher than 3-ring inserted product was found to increase with higher loading of cycloalkene.

GC and GC-MS Analysis of ROCM Products:

Well defined olefins were run under ROCM conditions with cyclic olefins to yield higher molecular weight products. GC and GC-MS analysis of these products identified up to 3 cyclic ring inserted compounds. The ring inserted products were characterized by GC and their molecular weights were determined by GC-MS analysis. The detection limit of our GC and GC-MS was n=3; when n>3 higher molecular weight products did not elute as sharp interpretable peaks. The n>3 value represents high molecular products that were not identified by GC or GC-MS, this value was calculated by 100% minus percent unreacted starting minus n=1, n=2 and n=3 percentages. The data below demonstrates the product distributions for the ratios of starting materials indicated.

I. GC Results of ROCM of 9-Octadecene (9C18) and Cyclooctene and Cyclododecene.

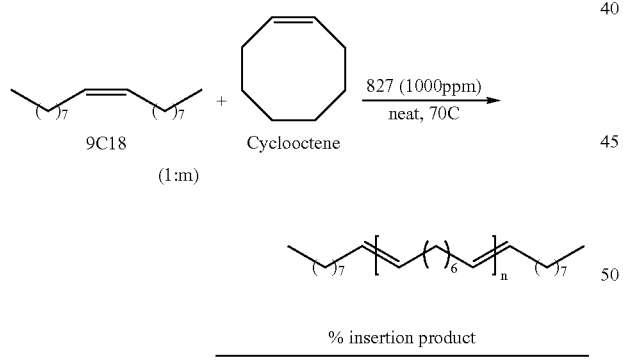

Scheme 6

| m | % SM[a] | n = 1 | n = 2 | n = 3 | n>3 |
|---|---|---|---|---|---|
| 0.5 | 42 | 14 | 2 | <1 | 42 |
| 1 | 49 | 19 | 8 | 4 | 20 |
| 2 | 31 | 20 | 9 | <1 | 40 |
| 3 | 23 | 17 | 11 | 1 | 48 |
| 5 | 15 | 11 | 7 | 1 | 66 |
| 10 | 14 | 6 | 4 | <1 | 77 |

[a]% SM represents the amount of unreacted starting acyclic olefin present at the end of the reaction.

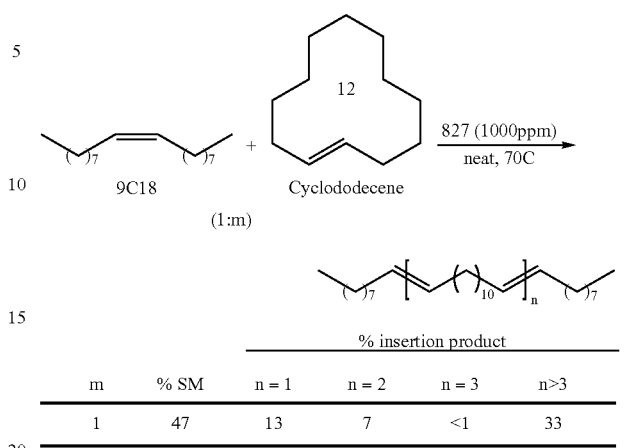

Scheme 7

| m | % SM | n = 1 | n = 2 | n = 3 | n>3 |
|---|---|---|---|---|---|
| 1 | 47 | 13 | 7 | <1 | 33 |

FIG. 1 depicts a typical GC-MS chromatogram of ROCM (n=1) products. The peaks at 20.10 min to 20.40 min are cis and trans-isomers of the n=1 ROCM product. The molecular weights of these peaks were determined to be 362, which corresponds to the product.

FIG. 2 depicts the MALD-TOF study of 9C18 and COE ROCM reactions. The reaction was run in a potassium salt matrix which explains why the molecular weights are 56 units higher than expected. The data clearly shows that each 110 repeat unit (when n=1 to 7) corresponds to another insertion of COE. With this technique, repeat units of up to n=7 COE inserted units have been identified. The GC-MS and MALDI-TOF data clearly demonstrated that the COE units are being inserted into the 9-octadecene to produce the desired ROCM high molecular weight products.

II. GC Results of ROCM of 1,18-Dimethyl esters of 9-Octadecene (9C18-diester) with Cyclooctene, Cyclododecene or Norbornene Ethylene Glycol Ester (NBE).

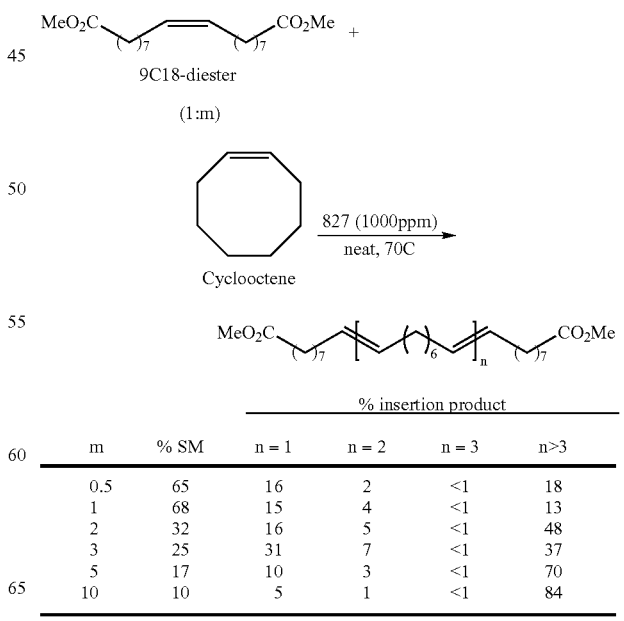

Scheme 8

| m | % SM | n = 1 | n = 2 | n = 3 | n>3 |
|---|---|---|---|---|---|
| 0.5 | 65 | 16 | 2 | <1 | 18 |
| 1 | 68 | 15 | 4 | <1 | 13 |
| 2 | 32 | 16 | 5 | <1 | 48 |
| 3 | 25 | 31 | 7 | <1 | 37 |
| 5 | 17 | 10 | 3 | <1 | 70 |
| 10 | 10 | 5 | 1 | <1 | 84 |

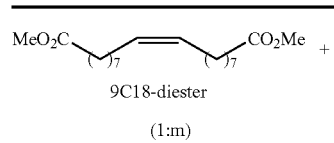

9C18-diester (1:m)

Scheme 9

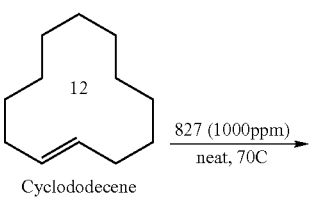

Cyclododecene

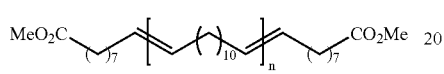

| | | % insertion product | | | |
|---|---|---|---|---|---|
| m | % SM | n = 1 | n = 2 | n = 3 | n>3 |
| 1 | 42 | 6 | 13 | <1 | 38 |

Scheme 10

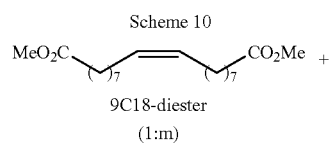

9C18-diester (1:m)

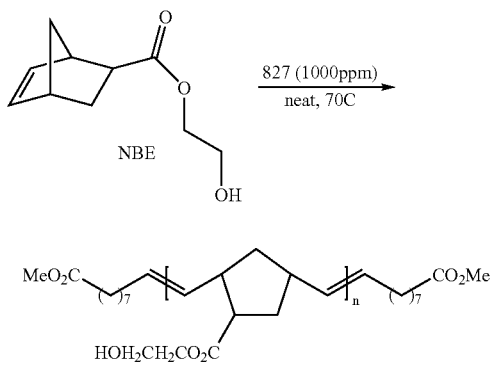

| | | % insertion product | | | |
|---|---|---|---|---|---|
| m | % SM | n = 1 | n = 2 | n = 3 | n>3 |
| 1 | 70 | 3 | <3 | <3 | 27 |

III. GC Results of ROCM of Methyl Oleate (MO) with Cyclooctene, Cyclododecene or Norbornene Ethylene Glycol Ester (NBE).

Scheme 11

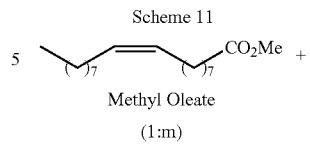

Methyl Oleate (1:m)

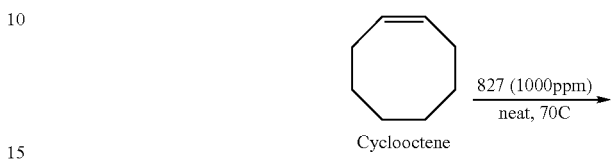

Cyclooctene

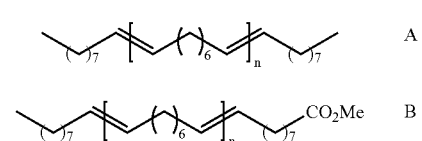

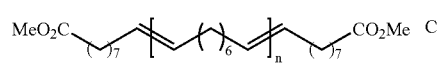

| | | % insertion product | | | |
|---|---|---|---|---|---|
| m | % SM | n = 1(A,B,C) | n = 2(A,B,C) | n = 3 | n>3 |
| 0.5 | 64 | 15(5,8,2) | 2(1,1,0) | 1 | 18 |
| 1 | 46 | 14(4,7,3) | 6(1,3,2) | 2 | 32 |
| 2 | 31 | 18(5,9,4) | 9(3,5,1) | 1 | 40 |
| 3 | 26 | 18(5,9,4) | 9(3,5,1) | 2 | 46 |
| 5 | 22 | 9(2,5,2) | 3(1,2,1) | 1 | 65 |
| 10 | 17 | 7(2,4,1) | 2(1,1,0) | <1 | 74 |

Scheme 12

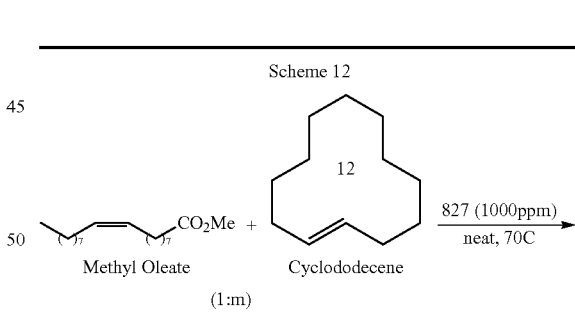

Methyl Oleate   Cyclododecene (1:m)

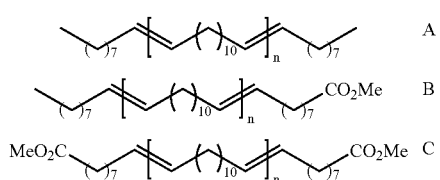

| | | % insertion product | | | |
|---|---|---|---|---|---|
| m | % SM | n = 1 | n = 2 | n = 3 | n>3 |
| 1 | 46 | 14 | 4 | <1 | 37 |

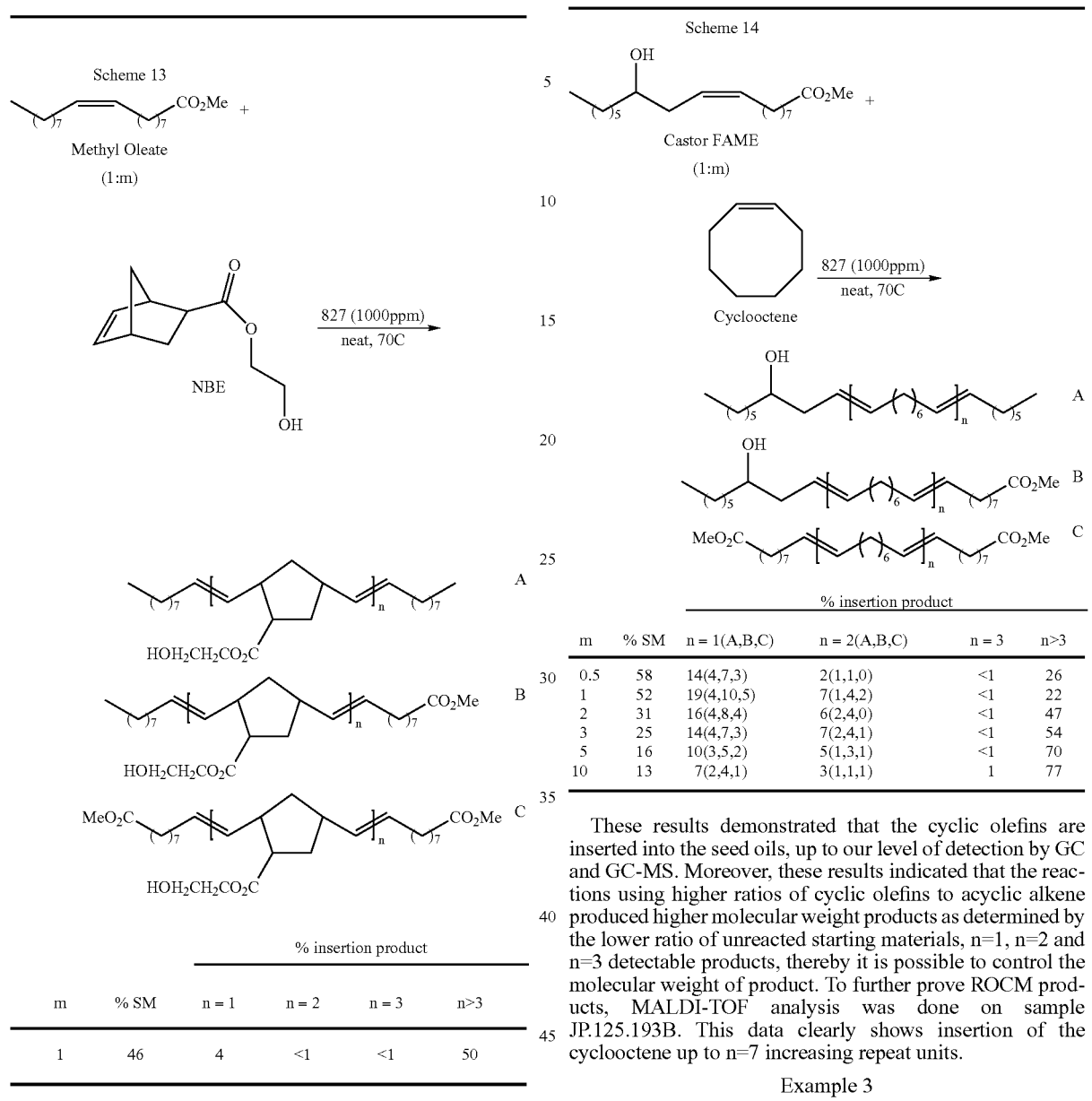

IV. GC Results of ROCM of Castor Oil Fatty Acid Methyl Ester (Castor Fame) with Cyclooctene These results demonstrated that the cyclic olefins are inserted into the seed oils, up to our level of detection by GC and GC-MS. Moreover, these results indicated that the reactions using higher ratios of cyclic olefins to acyclic alkene produced higher molecular weight products as determined by the lower ratio of unreacted starting materials, n=1, n=2 and n=3 detectable products, thereby it is possible to control the molecular weight of product. To further prove ROCM products, MALDI-TOF analysis was done on sample JP.125.193B. This data clearly shows insertion of the cyclooctene up to n=7 increasing repeat units.

Example 3

Using the General Metathesis procedure described above, various FAMEs were reacted with various cyclic olefins using the ruthenium alkylidene metathesis catalyst C827. The results are given in Table 2.

TABLE 2

Ring Opening Cross Metathesis Products

| Reaction # | FAME | Cyclic Olefin | Cyclic Olefin mol % | C827 (ppm) | FAME Conv.[1] (Y/N) | Cyclic Conv.[1] (Y/N) |
|---|---|---|---|---|---|---|
| JP.125.085 | MO | No | | 200 | Y | NA |
| JP.125.051M | ML | No | | 200 | Y | NA |
| JP.125.184G | None | NBM | | None | NA | NA |
| JP.125.184H | None | NBE | | None | NA | NA |
| JP.125.084K | None | Cydecanol | | None | NA | NA |
| JP.125.084E | None | NBM | | 200 | | Solid, no GC |
| JP.125.084F | None | NBE | | 200 | | Solid, no GC |
| CWL81-143 | None | Cydecanol | | 200 | | N |

TABLE 2-continued

Ring Opening Cross Metathesis Products

| Reaction # | FAME | Cyclic Olefin | Cyclic Olefin mol % | C827 (ppm) | FAME Conv.[1] (Y/N) | Cyclic Conv.[1] (Y/N) |
|---|---|---|---|---|---|---|
| JP.125.084A | MO | NBM | 50 | None | NA | NA |
| JP.125.084B | MO | NBE | 50 | None | NA | NA |
| JP.125.084I | MO | Cydecanol | 50 | None | NA | NA |
| JP.125.084C | ML | NBM | 50 | None | NA | NA |
| JP.125.084D | ML | NBE | 50 | None | NA | NA |
| JP.125.084J | ML | Cydecanol | 50 | None | NA | NA |
| JP.125.051A | MO | NBM | 50 | 200 | Y | Y |
| JP.125.051B | MO | NBM | 20 | 200 | Y | Y |
| JP.125.051C | MO | NBM | 10 | 200 | Y | Y |
| JP.125.051D | MO | NBE | 50 | 200 | Y | Y |
| JP.125.051E | MO | NBE | 20 | 200 | Y | Y |
| JP.125.051F | MO | NBE | 10 | 200 | Y | Y |
| CWL81-143A | MO | Cydecanol | 50 | 200-100 | Y | N |
| JP.125.051G | ML | NBM | 50 | 200 | Y | Y |
| JP.125.051H | ML | NBM | 20 | 200 | Y | Y |
| JP.125.051I | ML | NBM | 10 | 200 | Y | Y |
| JP.125.051H | ML | NBE | 50 | 200 | Y | Y |
| JP.125.051K | ML | NBE | 20 | 200 | Y | Y |
| JP.125.051L | ML | NBE | 10 | 200 | Y | Y |
| JP.125.066 | ML | Cydecanol | 50 | 200 | Y | N |

[1]Conv.: refers to whether metathesis occurred with each individual material; not a numerical value.

The data in Table 2 demonstrate that various FAMEs and cyclic olefins are good substrates for metathesis. However, cyclecanol was a poor substrate for metathesis under the standard reaction conditions (likely due to low ring strain) but did not negatively impact metathesis of other olefins with which it was mixed.

Example 4

Ring opening cross metathesis was carried out according to the General Metathesis Procedure using SBO and either NBM or NBE. The results are provided in Table 3. Conversion percent refers to the amount of new metathesis products formed as calculated by 100% minus the percent of unreacted starting materials.

The data demonstrates that NBM and NBE are substrates for ROCM reactions. The metathesis of neat SBO will reach 68% conversion at equilibrium. ROCM products are shown by the increased viscosity reading of the ROCM products compared to neat SBO.

Example 5

Ring opening cross metathesis was carried out according to the General Metathesis Procedure using SBO/F5L19 as olefinic substrate and Cydol as cyclic olefin. The results are provided in Table 4.

TABLE 3

Ring insertion cross metathesis of SBO with NBM or NBE

| Reaction # | Seed Oil/ Batch # | Cyclic Olefin | Cyclic olefin mol % | C827 (ppm) | Conv. (%) | Product a Solid[a] | Viscosity (cP)[b] |
|---|---|---|---|---|---|---|---|
| AV078-114C | SBO/F5L19 | — | 0 | 50 | 68 | N | 189 |
| JP.105.128 | SBO/F5L19 | NBM | 5 | 50 | 67 | | |
| JP.105.142 | SBO/F5L19 | NBM | 20 | 50 | 54 | | 198 |
| CWL81-108 | SBO/F5L19 | NBE | 5 | 50 | 69 | | 192 |
| CWL81-109A | SBO/F5L19 | NBE | 5 | 100 | 70 | | 132 |
| CWL81-109B | SBO/F5L19 | NBE | 10 | 50 | 69 | | 186 |
| CWL81-109C | SBO/F5L19 | NBE | 10 | 100 | 69 | | 240 |
| CWL81-110A | SBO/F5L19 | NBE | 20 | 50 | 67 | | 230 |
| CWL81-110B | SBO/F5L19 | NBE | 20 | 100 | 69 | | 276 |
| JP.105.171 | SBO/F5L19 | NBE | 35 | 100 | 67 | Y | |
| JP.105.172 | SBO/F5L19 | NBE | 50 | 100 | 68 | Y | 3780 |
| JP.105.184 | SBO/F5L19 | NBE | 100 | 100 | 62 | Y | |
| JP.105.160 | SBO/F5L19 | NBE | 200 | 400 | 70 | Y | |

[a]Metathesis product was a solid or precipitated.
[b]Viscosities were measured at 30–40 C. using S62 spindle with Brookfield DV-II+ viscometer

TABLE 4

Ring opening cross metathesis of SBO and Cydol

| Reaction # | Cyclic Olefin mol % | C827 (ppm) | Conv. (%) | Viscosity (cP) |
|---|---|---|---|---|
| AV078-114C | 0 | 50 | 68 | 189 |
| JP.105.122 | 5 | 50 | 65 | 173 |
| JP.105.124 | 5 | 100 | 68 | 179 |
| JP.105.123 | 10 | 50 | 64 | |
| JP.105.125 | 10 | 100 | 67 | 160 |
| JP.105.126 | 20 | 50 | 63 | 179 |
| JP.105.127 | 20 | 100 | 68 | 170 |
| JP.105.173 | 35 | 100 | 63 | |
| JP.105.174 | 50 | 100 | 53 | |
| JP.105.161 | 100 | 200 | 68 | |
| JP.105.162 | 200 | 200 | 56 | |

Cydol is a poor substrate for metathesis ROCM applications but it does not have an inhibitory effect on the metathesis catalyst.

Cydol is a poor substrate for metathesis ROCM applications but it does not have an inhibitory effect on the metathesis catalyst.

Example 6

Ring opening cross metathesis was carried out according to the General Metathesis Procedure using SBO/F5L19 as olefinic substrate and with HNB, NBM and Cydol as cyclic olefins. The results are provided in Table 5.

TABLE 5

Ring insertion cross metathesis of SBO and HNB

| Reaction # | Cyclic Olefin | Cyclic Olefin mol % | C827 (ppm) | Conv. (%) |
|---|---|---|---|---|
| CWL81-124A | HNB/NBM | 10/0.2 | 50 | 69 |
| CWL81-124B | HNB/NBM | 10/1.0 | 50 | 69 |
| CWL81-126A | HNB/NBE | 10/1.0 | 50 | 70 |
| CWL81-126B | HNB/NBE | 20/1.0 | 50 | 70 |
| CWL81-127A | HNB/Cydol | 10/1.0 | 50 | 69 |
| CWL81-127B | HNB/Cydol | 20/1.0 | 50 | 68 |

HNB, NBE, NBM and Cydol do not have an inhibitory effect on the metathesis catalyst or the metathesis of SBO.

HNB, NBE, NBM and Cydol do not have an inhibitory effect on the metathesis catalyst or the metathesis of SBO.

Example 7

Ring opening cross metathesis was carried out according to the General Metathesis Procedure using SBO as olefinic substrate and BNB, NBM, NBE and Cydol as cyclic olefins. The results are provided in Table 6.

TABLE 6

Ring insertion cross metathesis of SBO and BNB

| Reaction # | Seed Oil/ Batch # | Cyclic Olefin | Cyclic Olefin mol % | C827 (ppm) | Conv. (%) |
|---|---|---|---|---|---|
| JP.125.064 | SBO/F6C13 | BNB/NBM | 100/20 | 200 | 67 |
| JP.125.065 | SBO/F6C13 | BNB/NBM | 200/20 | 300 | 66 |
| JP.125.013 | SBO/F5J26 | BNB/NBE | 50/10 | 100 | 69 |
| JP.125.014 | SBO/F5J26 | BNB/NBE | 100/10 | 100 | 66 |
| JP.125.015 | SBO/F5J26 | BNB/NBE | 100/20 | 200 | 68 |
| JP.125.016 | SBO/F5J26 | BNB/NBE | 200/20 | 300 | 67 |
| JP.125.026 | SBO/F5J26 | BNB/Cydol | 50/10 | 100 | 69 |
| JP.125.027 | SBO/F5J26 | BNB/Cydol | 100/10 | 100 | 68 |
| JP.125.028 | SBO/F5J26 | BNB/Cydol | 100/20 | 200 | 69 |
| JP.125.029 | SBO/F5J26 | BNB/Cydol | 200/20 | 300 | 68 |

BNB, NBM, NBE and Cydol do not have an inhibitory effect on the metathesis catalyst.

Example 8

Ring opening cross metathesis was carried out according to the General Metathesis Procedure using SBO as olefinic substrate and COE, NBM, NBE and Cydol as the cyclic olefins. The results are provided in Table 7.

TABLE 7

Ring insertion cross metathesis of SBO and COE

| Reaction # | Seed Oil/ Batch # | Cyclic Olefin | Cyclic Olefin mol % | C827 (ppm) | Conv. (%) | Viscosity (cP) |
|---|---|---|---|---|---|---|
| JP.105.155 | SBO/F5L19 | COE/NBM | 10/1.0 | 50 | 64 | |
| JP.125.052 | SBO/F6C13 | COE/NBM | 50/10 | 100 | 70 | |
| JP.125.054 | SBO/F6C13 | COE/NBM | 100/20 | 200 | 71 | |
| JP.125.055 | SBO/F6C13 | COE/NBM | 200/20 | 300 | 73 | 256 |
| CWL81-129A | SBO/F5L19 | COE/NBE | 10/1.0 | 50 | 70 | |
| CWL81-129B | SBO/F5L19 | COE/NBE | 20/1.0 | 50 | 70 | |
| CWL81-136B | SBO/F5L19 | COE/NBE | 50/1.0 | 100 | 72 | 179 |
| JP.105.208 | SBO/F5J26 | COE/NBE | 50/10 | 100 | 68 | |
| CWL81-136A | SBO/F5L19 | COE/NBE | 100/10 | 100 | 71 | |
| JP.125.017 | SBO/F5J26 | COE/NBE | 100/20 | 200 | 70 | |
| JP.125.018 | SBO/F5J26 | COE/NBE | 200/20 | 200 | 76 | 468 |
| CWL81-128A | SBO/F5L19 | COE/Cydol | 10/1.0 | 50 | 69 | |
| CWL81-128B | SBO/F5L19 | COE/Cydol | 20/1.0 | 50 | 69 | |
| CWL81-135B | SBO/F5L19 | COE/Cydol | 50/1.0 | 100 | 72 | |
| CWL81-137B | SBO/F5L19 | COE/Cydol | 50/10 | 100 | 71 | |
| CWL81-135A | SBO/F5L19 | COE/Cydol | 100/10 | 100 | 71 | |
| CWL81-137A | SBO/F5L19 | COE/Cydol | 100/20 | 100 | 71 | |
| JP.105.198 | SBO/F5L19 | COE/Cydol | 200/20 | 100 | 72 | |

COE, NBM, and NBE readily participate in ROCM reactions as indicated by their increased viscosity measurements and do not have an inhibitory effect on the metathesis catalyst.

Example 9

Ring insertion cross metathesis was carried out according to the General Metathesis Procedure using SBO as olefinic substrate and CDDE, NBE and Cydol as the cyclic olefins. The results are provided in Table 8.

TABLE 8

Ring opening cross metathesis of SBO and CDDE

| Reaction # | Seed Oil/ Batch # | Cyclic Olefin | Cyclic Olefin mol % | C827 (ppm) | Conv. (%) | Viscosity (cP)a |
|---|---|---|---|---|---|---|
| JP.125.025 | SBO/F5J26 | CDDE/NBE | 50/10 | 100 | 67 | |
| JP.125.019 | SBO/F5J26 | CDDE/NBE | 100/20 | 100 | 68 | |
| JP.125.020 | SBO/F5J26 | CDDE/NBE | 200/20 | 200 | 74 | |
| JP.105.193 | SBO/F5L19 | CDDE/Cydol | 50/10 | 100 | 68 | |
| JP.105.194 | SBO/F5L19 | CDDE/Cydol | 100/10 | 200 | 68 | |
| JP.105.195 | SBO/F5L19 | CDDE/Cydol | 100/20 | 200 | 73 | |
| JP.105.197 | SBO/F5L19 | CDDE/Cydol | 200/20 | 200 | 75 | 800 |

CDDE readily participate in ROCM reactions as indicated by its increased viscosity measurement and does not have an inhibitory effect on the metathesis catalyst.

Example 10

Ring opening cross metathesis was carried out according to the General Metathesis Procedure using SBO as olefinic substrate and DCPD, NBM, NBE and Cydol as cyclic olefins. The results are provided in Table 9.

TABLE 9

Ring insertion cross metathesis of SBO and DCPD

| Reaction # | Seed Oil/ Batch # | Cyclic Olefin | Cyclic Olefin mol % | C827 (ppm) | Conv. (%) |
|---|---|---|---|---|---|
| JP.105.150 | SBO/F5L19 | DCPD/NBM | 10/1.0 | 50 | 63 |
| JP.105.151 | SBO/F5L19 | DCPD/NBM | 10/1.0 | 100 | 69 |
| JP.125.056 | SBO/F6C13 | DCPD/NBM | 50/10 | 100 | 65 |
| JP.125.057 | SBO/F6C13 | DCPD/NBM | 100/10 | 100 | 68 |
| JP.125.058 | SBO/F6C13 | DCPD/NBM | 100/20 | 200 | 67 |
| JP.125.059 | SBO/F6C13 | DCPD/NBM | 200/20 | 300 | 67 |
| JP.105.180 | SBO/F5L19 | DCPD/NBE | 10/1.0 | 100 | 68 |
| JP.105.181 | SBO/F5L19 | DCPD/NBE | 20/1.0 | 100 | 68 |
| JP.125.001 | SBO/F5J26 | DCPD/NBE | 50/10 | 100 | 68 |
| JP.125.002 | SBO/F5J26 | DCPD/NBE | 100/10 | 200 | 68 |
| JP.125.003 | SBO/F5J26 | DCPD/NBE | 100/20 | 200 | 67 |
| JP.125.004 | SBO/F5J26 | DCPD/NBE | 200/20 | 300 | 68 |
| JP.105.177 | SBO/F5L19 | DCPD/Cydol | 10/1.0 | 100 | 68 |
| JP.105.178 | SBO/F5L19 | DCPD/Cydol | 20/1.0 | 100 | 67 |
| JP.105.188 | SBO/F5L19 | DCPD/Cydol | 50/5 | 100 | 67 |
| JP.105.189 | SBO/F5L19 | DCPD/Cydol | 50/10 | 100 | 69 |
| JP.105.191 | SBO/F5L19 | DCPD/Cydol | 100/10 | 200 | 71 |
| JP.105.192 | SBO/F5L19 | DCPD/Cydol | 100/20 | 200 | 69 |
| JP.105.207 | SBO/F5J26 | DCPD/Cydol | 200/20 | 400 | 73 |

DCPD, NBE, NBM and Cydol do not have an inhibitory effect on the metathesis catalyst.

Example 11

Ring insertion cross metathesis was carried out according to the General Metathesis Procedure using SBO/F5J26 as olefinic substrate and CDTE, NBE and Cydol as olefinic substrates. The results are provided in Table 10.

TABLE 10

Ring insertion cross metathesis of SBO and CDTE

| Reaction # | Cyclic Olefin | Cyclic Olefin mol % | C827 (ppm) | Conv. (%) |
|---|---|---|---|---|
| JP.125.007 | CDTE/NBE | 100/20 | 200 | 74 |
| JP.125.008 | CDTE/NBE | 200/20 | 400 | 75 |
| JP.125.009 | CDTE/Cydol | 50/10 | 100 | 71 |
| JP.125.010 | CDTE/Cydol | 100/10 | 200 | 74 |
| JP.125.011 | CDTE/Cydol | 100/20 | 200 | 74 |
| JP.125.012 | CDTE/Cydol | 200/20 | 300 | 75 |

CDTE, NBE and Cydol do not have an inhibitory effect on the metathesis catalyst.

Example 12

Ring opening cross metathesis was carried out according to the General Metathesis Procedure using lights removed metathesized soybean oil (RMSBO) as olefinic substrate and various cyclic olefins. The results are provided in Table 11.

RMSBO is produced by metathesizing SBO to 68% conversion, then removing the lights under high vacuum while heating to 200° C. This process removes ~8 wt % of light hydrocarbons from the reaction.

TABLE 11

Ring opening cross metathesis of RMSBO and Cyclic Olefins

| Reaction # | Cyclic Olefin | Cyclic Olefin mol % | C827 (ppm) | Conv. (%) | Product a Solid[a] | Ratio of 9C$_{15}$ ester to palmitate[b] |
|---|---|---|---|---|---|---|
| RLP 66-084 | none | 0 | 50 | 68 | no | 1.40 |
| CWL81-133 | COE/NBM | 10/1.0 | 50 | 67 | | |
| JP.125.068 | COE/NBM | 50/10 | 100 | 66 | | 0.72 |
| JP.125.069 | COE/NBM | 100/10 | 100 | 71 | Y (clear elastic) | 0.44 |
| JP.125.070 | COE/NBM | 100/20 | 200 | 73 | | 0.40 |
| JP.125.071 | COE/NBM | 200/20 | 300 | 73 | Y (clear elastic) | 0.38 |
| CWL81-130 | COE/NBE | 10/1.0 | 50 | 66 | | |
| JP.125.072 | COE/NBE | 50/10 | 100 | 71 | | 0.57 |
| JP.125.087 | COE/NBE | 100/5 | 100 | 72 | | 0.42 |
| JP.125.073[c] | COE/NBE | 100/10 | 100 | 74 | | 0.43 |
| JP.125.074 | COE/NBE | 100/20 | 200 | 72 | | 0.39 |
| JP.125.075 | COE/NBE | 200/20 | 300 | 73 | | 0.29 |
| JP.105.200 | COE/Cydol | 100/5 | 200 | 70 | Y (elastic) | 0.47 |
| JP.105.201 | COE/Cydol | 50/10 | 200 | 67 | | 0.87 |
| JP.105.202 | COE/Cydol | 100/20 | 200 | 70 | Y (elastic) | 0.62 |
| JP.105.203 | COE/Cydol | 200/20 | 200 | 72 | Y (elastic) | 0.44 |
| JP.125.129 | CDDE/NBE | 50/10 | 100 | 70 | | 0.95 |
| JP.125.130 | CDDE/NBE | 100/10 | 100 | 69 | | 0.89 |
| JP.125.131 | CDDE/NBE | 100/20 | 200 | 72 | | 0.70 |
| JP.125.132 | CDDE/NBE | 200/20 | 400 | 76 | | 0.41 |
| JP.125.088 | DCPD/NBE | 100/5 | 100 | 72 | | 1.39 |
| JP.125.080 | DCPD/NBE | 50/10 | 100 | 92? | | 1.23 |
| JP.125.081 | DCPD/NBE | 100/10 | 200 | 69 | | 1.41 |
| JP.125.082 | DCPD/NBE | 100/20 | 300 | 71 | | 0.97 |
| JP.125.083 | DCPD/NBE | 200/20 | 400 | 69 | Y (white wax) | 1.27 |
| JP.125.089 | DCPD/Cydol | 100/5 | 200 | 69 | | 1.02 |
| JP.125.076 | DCPD/Cydol | 50/10 | 100 | 85? | | 0.53 |
| JP.125.077 | DCPD/Cydol | 100/10 | 200 | 69 | | 1.36 |
| JP.125.078 | DCPD/Cydol | 100/20 | 300 | 68 | | 1.21 |
| JP.125.079 | DCPD/Cydol | 200/20 | 400 | 70 | Y (white wax) | 1.16 |

[a]Metathesis product was a solid or precipitated.
[b]Ratio of 9C15ester to palmitate uses palmitate as an internal standard to determine the conversion of SBO to ROCM products. The 9C15 ester is consistently produced in SBO metathesis reactions. Plamitate is inert to metathesis and is easy intergrate by GC, therefore it is an ideal internal standard in these SBO metathesis reactions.
[c]Viscosity of sample was 14300 cP COE, NBM, NBE, Cydol and DCPD do not have an inhibitory effect on the metathesis catalyst. The decrease in the 9C15 ester to palmitate ratio indicates that the cyclic olefins are ring opening cross metathesizing with SBO to form new products.

Example 13

Ring opening cross metathesis was carried out according to the General Metathesis Procedure using castor oil as olefinic substrate and HNB, BNB, COE, DCPD and CDDE as cyclic olefins. The results are provided in Table 12.

TABLE 12

Ring opening cross metathesis of Caster Oil and Cyclic Olefins

| Reaction # | Cyclic Olefin | Cyclic Olefin mol % | C827 (ppm) | Conv. (%) |
|---|---|---|---|---|
| JP.105.139 | HNB | 20 | 200 | 58 |
| JP.105.140 | HNB | 20 | 400 | 57 |
| JP.125.037 | BNB | 50 | 200 | 58 |
| JP.125.038 | BNB | 100 | 200 | 59 |
| JP.125.039 | BNB | 200 | 400 | 58 |
| JP.105.133 | COE | 5 | 100 | 46 |
| JP.105.134 | COE | 5 | 200 | 55 |
| JP.105.136 | COE | 10 | 100 | 46 |
| JP.105.135 | COE | 10 | 200 | 56 |
| CWL81-115A | COE | 20 | 100 | 42 |
| CWL81-115B | COE | 20 | 200 | 58 |
| CWL81-115C | COE | 20 | 400 | 59 |
| JP.125.035 | COE | 50 | 200 | 62 |
| JP.105.163 | COE | 100 | 200 | 62 |
| JP.105.164 | COE | 200 | 400 | 75 |
| JP.105.144 | DCPD | 10 | 200 | 61 |
| JP.105.145 | DCPD | 20 | 400 | 59 |
| JP.125.032 | DCPD | 50 | 200 | 56 |
| JP.125.033 | DCPD | 100 | 200 | 54 |
| JP.125.034 | DCPD | 200 | 400 | 43 |
| CWL81-117C | CDDE | 10 | 200 | 53 |
| CWL81-117A | CDDE | 20 | 200 | 56 |
| CWL81-117B | CDDE | 20 | 400 | 59 |
| CWL81-142 | none | N/A | 200 | 58 |

HNB, BNB, COE, DCPD and CDDE do not have an inhibitory effect on the metathesis catalyst.

Example 14

Ring opening cross metathesis was carried out according to the General Metathesis Procedure using SBO/F5J26 as olefinic substrate and COE, CDDE, DCPD, CDTE and ENB as cyclic olefins. The results are provided in Table 13.

TABLE 13

Ring insertion cross metathesis of SBO and Cyclic Olefins

| Reaction # | Cyclic Olefin | Cyclic Olefin mol % | C827 (ppm) | Conv. (%) |
|---|---|---|---|---|
| JU-108-046 | COE | 20 | 50 | 66 |
| JU-108-047 | COE | 50 | 50 | 67 |
| JU-108-048 | COE | 100 | 100 | 71 |
| JU-108-049 | COE | 200 | 100 | 68 |
| JU-108-056 | CDDE | 5 | 50 | 66 |
| JU-108-057 | CDDE | 10 | 50 | 64 |
| JU-108-058 | CDDE | 20 | 50 | 72 |
| JU-108-059 | CDDE | 50 | 50 | 63 |
| JU-108-060 | CDDE | 100 | 100 | 68 |
| JU-108-061 | CDDE | 200 | 100 | 67 |
| JU-108-062 | DCPD | 5 | 50 | 67 |
| JU-108-063 | DCPD | 10 | 50 | 76 |
| JU-108-064 | DCPD | 20 | 50 | 72 |
| JU-108-065 | DCPD | 50 | 50 | 72 |
| JU-108-066 | DCPD | 100 | 100 | 69 |
| JU-108-067 | DCPD | 200 | 100 | 69 |
| JU-108-050 | CDTE | 5 | 50 | 68 |
| JU-108-051 | CDTE | 10 | 50 | 68 |
| JU-108-052 | CDTE | 20 | 50 | 69 |
| JU-108-053 | CDTE | 50 | 50 | 66 |
| JU-108-054 | CDTE | 100 | 100 | 73 |
| JU-108-055 | CDTE | 200 | 100 | 75 |
| JU-108-090 | ENB | 20 | 50 | 73 |
| JU-108-091 | ENB | 50 | 50 | 82 |
| JU-108-092 | ENB | 100 | 100 | 74 |
| JU-108-093 | ENB | 200 | 100 | 78 |

COE, CDDE, DCPD, CDTE and ENB do not have any inhibitory effect on the metathesis catalyst.

COE, CDDE, DCPD, CDTE and ENB do not have an inhibitory effect on the metathesis catalyst.

Example 15

Ring opening cross metathesis was carried out according to the General Metathesis Procedure using RMSBO as olefinic substrate and COE, CDDE, DCPD, CDTE and ENB as cyclic olefins. The results are provided in Table 14.

TABLE 14

Ring insertion cross metathesis of RMSBO and Cyclic Olefins

| Reaction # | Cyclic Olefin | Cyclic Olefin mol % | C827 (ppm) | Conv. (%) | Product a Solid[a] | Ratio of 9C15 ester to palmitate |
|---|---|---|---|---|---|---|
| RLP 66-084 | none | 0 | 50 | 68 | No | 1.40 |
| JU-108-044 | COE | 5 | 50 | 66 | | 1.16 |
| JU-108-045 | COE | 10 | 50 | 66 | | 1.08 |
| JU-108-068 | COE | 20 | 50 | 77 | | 0.59 |
| JU-108-069 | COE | 50 | 50 | 73 | | 0.51 |
| JU-108-070 | COE | 100 | 100 | solid | Y | |
| JU-108-071 | COE | 200 | 100 | solid | Y | |
| JU-108-094 | CDDE | 50 | 50 | — | | |
| JU-108-095 | CDDE | 100 | 100 | 73 | | 0.42 |
| JU-108-096 | CDDE | 200 | 100 | 73 | Y | 0.34 |
| JU-108-078 | DCPD | 5 | 50 | 76 | | 0.81 |
| JU-108-079 | DCPD | 10 | 50 | 73 | | 0.78 |
| JU-108-080 | DCPD | 20 | 50 | 73 | | 0.59 |
| JU-108-081 | DCPD | 50 | 50 | 68 | | |
| JU-108-082 | DCPD | 100 | 100 | 72 | | |
| JU-108-083 | DCPD | 200 | 100 | solid | Y | |
| JU-108-072 | CDTE | 5 | 50 | 71 | | 0.66 |
| JU-108-073 | CDTE | 10 | 50 | 71 | | 0.64 |
| JU-108-074 | CDTE | 20 | 50 | 72 | | 0.55 |
| JU-108-075 | CDTE | 50 | 50 | 69 | | 0.49 |
| JU-108-076 | CDTE | 100 | 100 | solid | Y | |
| JU-108-077 | CDTE | 200 | 100 | solid | Y | |
| JU-108-084 | ENB | 5 | 50 | 79 | | 0.74 |
| JU-108-085 | ENB | 10 | 50 | 75 | | 0.70 |
| JU-108-086 | ENB | 20 | 50 | 76 | | 0.73 |
| JU-108-087 | ENB | 50 | 50 | 77 | | 0.70 |
| JU-108-088 | ENB | 100 | 100 | 74 | | 1.06 |
| JU-108-089 | ENB | 200 | 100 | 81 | | 1.08 |

[a]Metathesis product was a solid or precipitated.

COE, CDDE, DCPD, CDTE and ENB do not have an inhibitory effect on the metathesis catalyst. The decrease in the 9C15 ester to palmitate ratio indicates that the cyclic olefins are ring opening cross metathesizing with SBO to form new products.

Example 16

Ring opening cross metathesis was carried out according to the General Metathesis Procedure using various olefinic substrates and cyclic olefins. The results are provided in Table 15.

TABLE 15

Ring insertion cross metathesis of SBO (batch F5L19) or RMSBO with Cyclic Olefins

| Reaction # | Seed Oil | Cyclic Olefin | Cyclic Olefin mol % | C827 (ppm) | Conv. (%) | Solidified[a] |
|---|---|---|---|---|---|---|
| JU-108-042 | SBO | COE | 5 | 50 | 69 | |
| JU-108-043 | SBO | COE | 10 | 50 | 69 | |
| JU-108-046 | SBO | COE | 20 | 50 | 66 | |
| JU-108-047 | SBO | COE | 50 | 50 | 67 | |
| JU-108-048 | SBO | COE | 100 | 100 | 71 | |
| JU-108-049 | SBO | COE | 200 | 100 | 68 | |
| JU-108-056 | SBO | CDDE | 5 | 50 | 66 | |
| JU-108-057 | SBO | CDDE | 10 | 50 | 64 | |
| JU-108-058 | SBO | CDDE | 20 | 50 | 72 | |
| JU-108-059 | SBO | CDDE | 50 | 50 | 63 | |
| JU-108-062 | SBO | DCPD | 5 | 50 | 67 | |
| JU-108-063 | SBO | DCPD | 10 | 50 | 76 | |
| JU-108-064 | SBO | DCPD | 20 | 50 | 72 | |
| JU-108-065 | SBO | DCPD | 50 | 50 | 72 | |
| JU-108-066 | SBO | DCPD | 100 | 100 | 69 | |
| JU-108-067 | SBO | DCPD | 200 | 100 | 69 | |
| JU-108-050 | SBO | CDTE | 5 | 50 | 68 | |
| JU-108-051 | SBO | CDTE | 10 | 50 | 68 | |
| JU-108-052 | SBO | CDTE | 20 | 50 | 69 | |
| JU-108-053 | SBO | CDTE | 50 | 50 | 66 | |

TABLE 15-continued

Ring insertion cross metathesis of SBO (batch F5L19) or RMSBO with Cyclic Olefins

| Reaction # | Seed Oil | Cyclic Olefin | Cyclic Olefin mol % | C827 (ppm) | Conv. (%) | Solidified[a] |
|---|---|---|---|---|---|---|
| JU-108-054 | SBO | CDTE | 100 | 100 | 73 | |
| JU-108-055 | SBO | CDTE | 200 | 100 | 75 | |
| JU-108-044 | RMSBO | COE | 5 | 50 | 66 | |
| JU-108-045 | RMSBO | COE | 10 | 50 | 66 | |
| JU-108-068 | RMSBO | COE | 20 | 50 | 77 | |
| JU-108-069 | RMSBO | COE | 50 | 50 | 73 | |
| JU-108-070 | RMSBO | COE | 100 | 100 | — | Yes[b] |
| JU-108-071 | RMSBO | COE | 200 | 100 | — | Yes[b] |
| JU-108-072 | RMSBO | CDTE | 5 | 50 | 71 | |
| JU-108-073 | RMSBO | CDTE | 10 | 50 | 71 | |
| JU-108-074 | RMSBO | CDTE | 20 | 50 | 72 | |
| JU-108-075 | RMSBO | CDTE | 50 | 50 | 69 | |
| JU-108-076 | RMSBO | CDTE | 100 | 100 | — | Yes[b] |
| JU-108-077 | RMSBO | CDTE | 200 | 100 | — | Yes[b] |
| JU-108-078 | RMSBO | DCPD | 5 | 50 | 76 | |
| JU-108-079 | RMSBO | DCPD | 10 | 50 | 73 | |
| JU-108-080 | RMSBO | DCPD | 20 | 50 | 73 | |
| JU-108-081 | RMSBO | DCPD | 50 | 50 | 68 | |
| JU-108-082 | RMSBO | DCPD | 100 | 100 | 72 | No[c] |
| JU-108-083 | RMSBO | DCPD | 200 | 100 | — | Yes[c] |
| CWL-81-100 | MO | COD monoxide | 100 | 50[d] | 29 | |
| JP-105.086 | SBO | COD monoxide | 100 | 450 | 10 | |

[a]Metathesis product was a solid or precipitated.
[b]Clear jelly.
[c]White, opaque.
[d]Catalyst 627 used COE, CDDE, DCPD, and CDTE do not have an inhibitory effect on the metathesis catalyst. COD monoxide has an inhibitory effect on metathesis catalysts 827 and 627.

Example 17

Ring insertion cross metathesis was carried out according to the General Metathesis Procedure using various seed oils and COE as cyclic olefin. The results are provided in Table 16.

TABLE 16

Ring insertion cross metathesis of Seed Oils with COE

| Lot # | Seed Oil | Cyclic Olefin mol % | C827 (ppm) | Conv. at 2 hr (%) | Conv. at 17 hr (%) | Solidified[a] |
|---|---|---|---|---|---|---|
| JP.125.146 | Canola | 80 | 730 | 70 | 68 | |
| JP.125.147 | Corn | 79 | 740 | 75 | 75 | |
| JP.125.148 | Peanut | 80 | 740 | 63 | 65 | |
| JP.125.149 | Safflower | 80 | 740 | 84 | 83 | |
| JP.125.150 | Olive | 80 | 740 | 60 | 61 | |
| JP.125.151 | Jojoba | 55 | 510 | 75 | | Y |
| JP.125.152 | Meadowfoam | 85 | 790 | 79 | 79 | Y |

[a]Metathesis product was a solid or precipitated.

All of the seed oils in Table 16 and COE are substrates for ROCM reactions.

Example 18

Ring insertion cross metathesis was carried out according to the General Metathesis Procedure using SBO/F6C13 as olefinic substrate, COE (100 mol %) as cyclic olefin, and various metathesis catalysts. The results are provided in Table 17.

TABLE 17

Ring insertion cross metathesis of SBO and Cyclooctene[a] with various catalysts

| Entry | Lot # | Metathesis Catalyst | Catalyst Loading (ppm) | Conv. at 2 hr (%) | Conv. at 18 hr (%) |
|---|---|---|---|---|---|
| 1 | JP.125.136 | 823 | 1000 | N/D | 51 |
| 2 | JP.125.137 | 601 | 1000 | N/D | 38 |
| 3 | JP.125.138 | 801 | 1000 | N/D | 40 |
| 4 | JP.125.139 | 838 | 1000 | N/D | 15 |
| 5 | JP.125.140 | 701 | 1000 | N/D | 36 |

TABLE 17-continued

Ring insertion cross metathesis of SBO and Cyclooctene[a] with various catalysts

| Entry | Lot # | Metathesis Catalyst | Catalyst Loading (ppm) | Conv. at 2 hr (%) | Conv. at 18 hr (%) |
|---|---|---|---|---|---|
| 6 | JP.125.141 | 848 | 500 | 68 | 72 |
| 7 | JP.125.142 | 627 | 500 | 75 | 74 |
| 8 | JP.125.143 | 697 | 500 | 27 | 29 |
| 9 | JP.125.144 | 933 | 500 | 72 | 73 |
| 10 | JP.125.145 | 712 | 500 | 74 | 74 |

[a] 1 mol of COE per 1 mol of SBO.

This data shows that a wide variety of metathesis catalysts will metathesize seed oil ROCM reactions.

Example 19

Ring insertion cross metathesis was carried out according to the General Metathesis Procedure using a chain transfer agent with a seed oil and a cyclic olefin using 827 metathesis catalyst. The results are provided in Table 18.

The goals of these experiments were to develop reaction conditions that yielded cyclic olefin inserted products that were terminated by the chain transfer agent. Percent Conversion (% Convers.) is defined as the percent of substrate that has been converted to another metathesis product (ie 66% conversion represents new metathesis products with 34% unreacted substrate).

TABLE 18

ROCM reactions with a chain transfer agent.

| Reaction # | Substrate[a] | Cyclic Olefin[a] | Chain transfer agent[a] | 827 (ppm) | Phase at 25° C. | % Conv. |
|---|---|---|---|---|---|---|
| JP.140.057A | SBO (1) | COE (3) | 9C18DE (3) | 2100 | liquid | — |
| JP.140.057B | SBO (1) | COE (6) | 9C18DE (3) | 2700 | liquid | |
| JP.140.057C | SBO (1) | COE (9) | 9C18DE (3) | 3300 | liquid | |
| JP.140.057D | SBO (1) | COE (15) | 9C18DE (3) | 3900 | solid | |
| JP.140.057E | SBO (1) | COE (20) | 9C18DE (3) | 5500 | solid | |
| JP.140.061A | 9C18DE (1) | COE (2) | VNB (2) | 1000 | liquid | |
| JP.140.061B | 9C18DE (1) | COE (4) | VNB (2) | 1400 | liquid | |
| JP.140.061C | 9C18DE (1) | COE (6) | VNB (2) | 1800 | solid | |
| JP.140.061D | 9C18DE (1) | COE (8) | VNB (2) | 2200 | solid | |
| JP.140.061E | 9C18DE (1) | COE (10) | VNB (2) | 2600 | solid | |
| JP.140.067A | Biodiesel (1) | COE (1) | BisTMS (1) | 1200 | liquid | 66 |
| JP.140.067B | Biodiesel (1) | COE (2) | BisTMS (1) | 1500 | liquid | 36 |
| JP.140.067C | Biodiesel (1) | COE (3) | BisTMS (1) | 1800 | liquid | 39 |
| JP.140.067D | Biodiesel (1) | COE (5) | BisTMS (1) | 2400 | liquid | 47 |
| JP.140.067E | Biodiesel (1) | COE (10) | BisTMS (1) | 3900 | liquid | 40 |
| JP.140.069A1 | SBO (1)[b] | COE (4.5) | BisTMS (3)[b] | 3600 | liquid | — |
| JP.140.069A2 | SBO (1)[b] | COE (9) | BisTMS (3)[b] | 4950 | liquid | |
| JP.140.069A3 | SBO (1)[b] | COE (13.5) | BisTMS (3)[b] | 6300 | liquid | |
| JP.140.069A4 | SBO (1)[b] | COE (22.5) | BisTMS (3)[b] | 9000 | liquid | |
| JP.140.069A5 | SBO (1)[b] | COE (45) | BisTMS (3)[b] | 15750 | liquid | |
| JP.140.069B1 | SBO (1) | COE (4.5) | BisTMS (3) | 3600 | liquid | |
| JP.140.069B2 | SBO (1) | COE (9) | BisTMS (3) | 4950 | liquid | |
| JP.140.069B3 | SBO (1) | COE (13.5) | BisTMS (3) | 6300 | solid/liquid | |
| JP.140.069B4 | SBO (1) | COE (22.5) | BisTMS (3) | 9000 | solid | |
| JP.140.069B5 | SBO (1) | COE (45) | BisTMS (3) | 15750 | solid | |
| JP.140.070A | SBO (1) | COD (2.25) | BisTMS (4.5) | 2025 | liquid | |
| JP.140.070B | SBO (1) | COD (4.5) | BisTMS (4.5) | 2625 | liquid | |
| JP.140.070C | SBO (1) | COD (6.75) | BisTMS (4.5) | 4725 | liquid | |
| JP.140.070D | SBO (1) | COD (11.25) | BisTMS (4.5) | 6375 | liquid | |
| JP.140.070E | SBO (1) | COD (22.5) | BisTMS (4.5) | 9450 | liquid | |
| JP.140.071A | Biodiesel (1) | COD (0.5) | BisTMS (1) | 1050 | liquid | |
| JP.140.071B | Biodiesel (1) | COD (1) | BisTMS (1) | 1200 | liquid | |
| JP.140.071C | Biodiesel (1) | COD (1.5) | BisTMS (1) | 1350 | liquid | |
| JP.140.071D | Biodiesel (1) | COD (2.5) | BisTMS (1) | 1650 | liquid | |
| JP.140.071E | Biodiesel (1) | COD (5) | BisTMS (1) | 2400 | liquid | |
| JP.140.073 | Biodiesel (1) | — | BisTMS (1) | 900 | N/A | 55 |
| JP.140.076A1 | Biodiesel (1) | COE (1) | BisTMS (1) | 1200 | liquid | 95 |
| JP.140.076A2 | Biodiesel (1) | COE (2) | BisTMS (1) | 1500 | liquid | 96 |
| JP.140.076A3 | Biodiesel (1) | COE (3) | BisTMS (1) | 1800 | liquid | 97 |
| JP.140.076A4 | Biodiesel (1) | COE (5) | BisTMS (1) | 2400 | liquid/solid | 98 |
| JP.140.076A5 | Biodiesel (1) | COE (10) | BisTMS (1) | 3900 | solid | 99 |
| JP.140.076B1 | Biodiesel (1) | COD (0.5) | BisTMS (1) | 1050 | liquid | 95 |
| JP.140.076B2 | Biodiesel (1) | COD (1) | BisTMS (1) | 1200 | liquid | 95 |
| JP.140.076B3 | Biodiesel (1) | COD (1.5) | BisTMS (1) | 1350 | liquid | 95 |
| JP.140.076B4 | Biodiesel (1) | COD (2.5) | BisTMS (1) | 1650 | liquid | 96 |
| JP.140.076B5 | Biodiesel (1) | COD (5) | BisTMS (1) | 2400 | liquid | 98 |
| JP.140.082 | Biodiesel (1) | — | BisTMS (1) | 900 | liquid | 88 |

[a] mole equivalents
[b] reacted chain transfer agent with substrate, then added cyclic olefin ROCM was accomplished using cyclic olefins with a chain transfer agent to produce novel metathesis products as determined by GC analysis and some of the products being solids.

Example 20

General procedure for the cross-metatheses of olefinic substrate and 1-butene: Terminal olefins were synthesized by the cross metathesis 1-butene and seed oils with a ruthenium metathesis catalyst. Seed oils include triacylglycerides, as in soybean oil, fatty acid esters, as in jojoba oil and FAMES, such as methyl esters of soybean oil (soy FAME).

1-Butene used was added to a Fisher-Porter bottle equipped with a stir bar and charged with the olefinic substrates. A solution of olefin metathesis catalyst of an appropriate concentration was prepared in anhydrous dichloromethane (obtained from Aldrich and degassed with Argon) and the desired volume of this solution added to the olefinic substrate. The head of the Fisher-Porter bottle was equipped with a pressure gauge and a dip-tube was adapted on the bottle. The system was sealed and taken out of the glove, box to a gas line. The vessel was then purged 3 times with 1-propene, pressurized to the indicated pressure (about 50 to about 150 psi for 1-propene) and placed in an oil bath at the indicated temperature. The reaction was monitored by GC analysis. The vial was sealed with a Teflon-seal cap and the olefinic substrate/alpha-olefin mixture was brought to the indicated temperature, so that the reactions are conducted under a slightly positive pressure (from 1.1 to about 2 atm, i.e. from 16 psi to about 30 psi). A solution of olefin metathesis catalyst of an appropriate concentration was prepared in anhydrous dichloromethane (obtained from Aldrich and degassed with Ar) and the desired volume of this solution added to the olefinic substrate/alpha-olefin mixture via syringe through the Teflon-seal while stirring. The reaction mixture was kept at the desired temperature for the indicated period of time before adding a 1.0 M solution of THMP (1 mL) via syringe through the Teflon-seal cap. The mixture was then heated at 60° C. for 1 hour, diluted with 5 mL of distilled water and 5 mL of hexanes and the organic phase was separated and analyzed by GC. If the olefinic substrate is a glyceride, it is transesterified to the methyl ester prior to GC analysis.

Propenolyzed Soybean oil (PSBO): To the metathesis catalyst removed product from above was added to a vacuum distillation setup. The pot was heated to 150° C. under high vacuum to remove volatiles. The pot was cooled to room temp and the propenoylzed SBO was used without further purification.

Ring insertion cross metathesis was carried out according to the General Metathesis Procedure using PSBO, a cyclic olefin and a chain using 827 metathesis catalyst loading. The results are provided in Table 19.

TABLE 19

ROCM reactions with PSBO, a cyclic olefin and a chain transfer agent.

| Reaction # | Seed Oil | Cyclic Olefin | Chain Transfer Agent | 827 (ppm) | Phase at 25° C. after Work up | % Conv |
|---|---|---|---|---|---|---|
| JP.140.085A | PSBO (1) | — | BisTBS (2) | 1500 | liquid | 71 |
| JP.140.085B | PSBO (1) | — | BisTBS (10) | 3900 | liquid/ppt | 90 |
| JP.140.085C | PSBO (1) | COE (2) | BisTBS (2) | 2100 | liquid | 85 |
| JP.140.085D | PSBO (1) | COD (1) | BisTBS (2) | 2100 | liquid | 85 |
| JP.140.085E | PSBO (1) | COD (2) | BisTBS (2) | 2100 | liquid/ppt | 93 |
| JP.140.085F | PSBO (1) | COE (4) | — | 2100 | very visc | 71 |
| JP.140.085G | PSBO (1) | COD (2) | — | 2100 | very visc | 89 |
| JP.140.085H | PSBO (1) | COD (4) | — | 2100 | solid | 81 |
| JP.140.086A | A | — | — | — | liquid | 71 |
| JP.140.086C | B | — | — | — | liquid | 85 |
| JP.140.086D | C | — | — | — | liquid | 85 |
| JP.140.087[a] | PSBO (1) | COE (4) | — | 2100 | liquid | 73 |
| JP.140.088[b] | PSBO (1) | — | BisTBS (10) | 3900 | liquid | 94 |
| JP.140.090 | PSBO (1) | COE (2) | BisTBS (2) | 2100 | ND | 96 |
| JP.140.091 | PSBO (1) | COE (2) | BisTBS (2) | 2100 | ND | 94 |
| JP.140.089 | 9DA (1) | COE (2) | BisTBS (1) | 1200 | ND | — |
| JP.140.092 | 9DA (1) | COD (2) | BisTBS (1) | 1500 | ND | — |
| JP.140.098A | PSBO (1) | COE (2) | — | 100 | ND | 74 |
| JP.140.098B | PSBO (1) | COE (2) | — | 200 | ND | 74 |
| JP.140.098C | PSBO (1) | COE (2) | — | 400 | ND | 74 |
| JP.140.098D | PSBO (1) | COD (2) | — | 140 | ND | 83 |
| JP.140.098E | PSBO (1) | COD (2) | — | 280 | ND | 83 |
| JP.140.098F | PSBO (1) | COD (2) | — | 560 | ND | 83 |
| JP.140.099 | PSBO (1) | COD (2) | — | 2100 | ND | 83 |
| JP.140.100 | PSBO (1) | COE (2) | — | 1500 | ND | 75 |
| JP.140.105A | PSBO (1) | COE (2) | — | 50 | ND | 68 |
| JP.140.105B | PSBO (1) | COE (2) | — | 125 | ND | 70 |
| JP.140.105C | PSBO (1) | COE (2) | — | 150 | ND | 69 |
| JP.140.105D | PSBO (1) | COD (2) | — | 70 | ND | 79 |
| JP.140.105E | PSBO (1) | COD (2) | — | 175 | ND | 79 |
| JP.140.105F | PSBO (1) | COD (2) | — | 210 | ND | 83 |

A = Deprotected product from JP.140.085A which was reanalyzed
B = Deprotected product from JP.140.085C which was reanalyzed
C = Deprotected product from JP.140.085D which was reanalyzed
[a]Scale Up of JP.140.085F
[b]Repeated JP.140.085B Propenolyzed soybean oil is a good substrate for ROCM reactions with cyclic olefins and a chain transfer agent. Good to high conversions were obtained in the reactions.

Example 21

Table 20 Contains GPC data for numerous ROCM reactions. The goal of this study was to understand the reaction conditions that would produce the desired ROCM products.

TABLE 20

GPC Data for ROCM Reactions using 827 metathesis catalysts.

| Notebook # | Substrate | Cyclic Olefin | Equiv of Cyclic Olefins to Substrate (mol/mol) | 827 (ppm) | Conv (%) | Mn | Mw | MP | PDI* |
|---|---|---|---|---|---|---|---|---|---|
| | | | | | | (Major Peak vs. PSS reported in Daltons) | | | |
| JP.140.009D | 9C18 | COE | 5 | 1000 | 85 | 2845 | 3645 | 3294 | 1.28 |
| JP.140.024A | 9C18 | COE | 10 | 1800 | 90 | 4072 | 6441 | 7368 | 1.58 |
| JP.140.024C | 9C18 | COE | 20 | 3500 | 96 | 8578 | 15840 | 15518 | 1.85 |
| JP.140.010E | 9C18DE | COE | 10 | 1800 | 90 | 2924 | 4487 | 3923 | 1.53 |
| JP.140.025B | 9C18DE | COE | 15 | 2700 | 94 | 5685 | 8504 | 8712 | 1.5 |
| JP.140.025C | 9C18DE | COE | 20 | 3500 | 96 | 7165 | 11265 | 11511 | 1.57 |
| JP.140.027A | MO | COE | 10 | 1800 | 84 | 3713 | 5922 | 6953 | 1.6 |
| JP.140.027B | MO | COE | 15 | 2700 | 95 | 6187 | 9219 | 9292 | 1.49 |
| JP.140.027C | MO | COE | 20 | 3500 | 96 | 6005 | 10416 | 11470 | 1.73 |
| JP.140.028A | CF | COE | 10 | 1800 | 80 | 4298 | 6258 | 6656 | 1.46 |
| JP.140.028B | CF | COE | 15 | 2700 | 87 | 6029 | 9057 | 9241 | 1.5 |
| JP.140.028C | CF | COE | 20 | 3500 | 90 | 7650 | 11677 | 12157 | 1.53 |
| JP.140.021F | Castor Oil | COE | 20 | 2000 | 84 | 5643 | 11222 | 21449 | 1.99 |
| JP.140.033A1 | 9C18 | COE | 5 | 1000 | 99 | 2581 | 3137 | 2786 | 1.22 |
| JP.140.033A2 | 9C18 | COE | 10 | 1800 | 98 | 3295 | 4964 | 5513 | 1.51 |
| JP.140.033A3 | 9C18 | COE | 20 | 3500 | 99 | 5426 | 9130 | 9954 | 1.68 |
| JP.140.033B1 | 9C18DE | COE | 10 | 1800 | NYD | 2735 | 4084 | 3796 | 1.49 |
| JP.140.033B2 | 9C18DE | COE | 15 | 2700 | NYD | 3738 | 5896 | 6710 | 1.58 |
| JP.140.033B3 | 9C18DE | COE | 20 | 3500 | NYD | 4630 | 7651 | 8454 | 1.65 |
| JP.140.033C1 | MO | COE | 10 | 1800 | 99 | 2949 | 4263 | 4125 | 1.45 |
| JP.140.033C2 | MO | COE | 15 | 2700 | 99 | 3970 | 6377 | 6921 | 1.61 |
| JP.140.033C3 | MO | COE | 20 | 3500 | 99 | 5025 | 9242 | 9495 | 1.84 |
| JP.140.039A | Castor FAME | — | — | — | — | 40 | 68 | 64 | 1.68 |
| JP.140.012A | CF | COE | 0.5 | 1000 | 42 | 38 | 79 | 77 | 2.07 |
| JP.125.206A | CF | COE | 1 | 1000 | 48 | 1239 | 1293 | 1059 | 1.05 |
| JP.140.012B | CF | COE | 2 | 1000 | 69 | 1711 | 1859 | 1322 | 1.09 |
| JP.140.012C | CF | COE | 3 | 1000 | 75 | 1879 | 2147 | 1758 | 1.14 |
| JP.140.012D | CF | COE | 5 | 1000 | 84 | 2021 | 2537 | 2367 | 1.25 |
| JP.140.033D1 | CF | COE | 10 | 1800 | 99 | 3089 | 4804 | 5601 | 1.55 |
| JP.140.033D2 | CF | COE | 15 | 2700 | 99 | 4050 | 6720 | 7267 | 1.66 |
| JP.140.033D3 | CF | COE | 20 | 3500 | 99 | 5852 | 9607 | 10030 | 1.64 |
| JP.140.039B | Castor Oil | — | — | — | — | 1442 | 1459 | 1486 | 1.01 |
| JP.140.036A | Castor Oil | — | — | 600 | ND | 11896 | 17024 | 31181 | 1.43 |
| JP.140.036B | Castor Oil | COE | 3 | 1200 | ND | 5345 | 8439 | 11887 | 1.58 |
| JP.140.036C | Castor Oil | COE | 9 | 2400 | ND | 3980 | 7707 | 13390 | 1.94 |
| JP.140.036D | Castor Oil | COE | 15 | 3600 | ND | 5141 | 8773 | 14238 | 1.71 |
| JP.140.044 | Castor Oil | COE | 20 | 4600 | ND | 8235 | 24287 | 54459 | 2.95 |
| JP.140.033E | Castor Oil | COE | 20 | 2000 | ND | 5563 | 18050 | 38940 | 3.24 |
| JP.140.036E | Castor Oil | COE | 30 | 6600 | ND | 8237 | 17364 | 32816 | 2.11 |
| JP.140.039C | — | COE | — | — | — | 75 | 90 | 94 | 1.19 |
| JP.140.003 | — | COE | — | 1000 | — | 4910 | 9626 | 7393 | 1.96 |
| JP.140.039D | C12 | — | — | — | — | | | 65 | |
| JP.140.037A | MO | COD | 1 | 600 | 91 | 44 | 397 | 86 | 8.98 |
| JP.140.037B | MO | COD | 5 | 1100 | 98 | 1187 | 2044 | 2196 | 1.72 |
| JP.140.037C | MO | COD | 10 | 2100 | 99 | 2752 | 3751 | 3725 | 1.36 |
| JP.140.037D | CF | COD | 1 | 600 | 66 | 523 | 719 | 286 | 1.37 |
| JP.140.037E | CF | COD | 5 | 1100 | 90 | 1849 | 2288 | 2201 | 1.25 |
| JP.140.037F | CF | COD | 10 | 2100 | 95 | 2642 | 3705 | 4010 | 1.4 |
| JP.140.038A | MO | PBD | 1 | 600 | 92 | 72 | 189 | 45 | 2.6 |
| JP.140.038B | MO | PBD | 5 | 1100 | 91 | 212 | 754 | 488 | 3.56 |
| JP.140.038C | MO | PBD | 10 | 2100 | 97 | 600 | 1350 | 1327 | 2.25 |
| JP.140.038D | CF | PBD | 1 | 600 | 54 | 28 | 187 | 29 | 6.59 |
| JP.140.038E | CF | PBD | 5 | 1100 | 76 | 541 | 945 | 568 | 1.75 |
| JP.140.038F | CF | PBD | 10 | 2100 | 92 | 582 | 1322 | 1368 | 2.27 |
| JP.140.041A1 | Castor Oil | COD | 3 | 1800 | ND | 4262 | 7773 | 12212 | 1.82 |
| JP.140.041B1 | Castor Oil | COD | 9 | 4200 | ND | 6309 | 11466 | 18572 | 1.82 |
| JP.140.041C1 | Castor Oil | COD | 15 | 6600 | ND | 4479 | 10619 | 20058 | 2.37 |
| JP.140.041D1 | Castor Oil | COD | 20 | 8600 | ND | 4022 | 10055 | 20165 | 2.5 |
| JP.140.041E1 | Castor Oil | COD | 30 | 12600 | ND | 6286 | 12014 | 21854 | 1.91 |

TABLE 20-continued

GPC Data for ROCM Reactions using 827 metathesis catalysts.

| Notebook # | Substrate | Cyclic Olefin | Equiv of Cyclic Olefins to Substrate (mol/mol) | 827 (ppm) | Conv (%) | Mn | Mw | MP | PDI* |
|---|---|---|---|---|---|---|---|---|---|
| | | | | | | | (Major Peak vs. PSS reported in Daltons) | | |
| JP.140.041A2 | Castor Oil | PBD | 3 | 1200 | ND | 3619 | 8122 | 7641 | 2.24 |
| JP.140.041B2 | Castor Oil | PBD | 9 | 2400 | ND | 5134 | 11159 | 9756 | 2.17 |
| JP.140.041C2 | Castor Oil | PBD | 15 | 3600 | ND | 5695 | 11684 | 10560 | 2.05 |
| JP.140.041D2 | Castor Oil | PBD | 20 | 4600 | ND | 2200 | 7417 | 8214 | 3.37 |
| JP.140.041E2 | Castor Oil | PBD | 30 | 6600 | ND | 2108 | 6933 | 7776 | 3.29 |
| JP.140.043A | 9C18 | — | — | — | ND | 338 | 340 | 338 | 1 |
| JP.140.043B | 9C18DE | — | — | — | ND | 421 | 424 | 425 | 1.01 |
| JP.140.043C | MO | — | — | — | ND | 382 | 387 | 381 | 1.01 |
| JP.140.043D | MO | — | — | 200 | ND | 381 | 386 | 383 | 1.01 |
| JP.140.043E | — | PBD | — | — | ND | 4938 | 8145 | 7320 | 1.65 |
| JP.140.043F | — | PBD | — | 200 | ND | 3379 | 8523 | 8020 | 2.52 |
| JP.140.043G | — | COD | — | — | ND | 490 | 493 | 500 | 1.01 |
| JP.140.043H | — | COD | — | 400 | ND | 34375 | 45119 | 53596 | 1.31 |
| JP.140.043I | SBO | — | — | — | ND | 1260 | 1270 | 1283 | 1.01 |
| JP.140.043J | SBO | — | — | 900 | ND | 7711 | 10422 | 6108 | 1.35 |
| JP.140.045 | CF | — | — | 200 | ND | 528 | 537 | 540 | 1.02 |
| JP.140.042 | Castor Oil | COD | 30 | 12600 | ND | 9769 | 30449 | 73647 | 3.12 |

The data demonstrate that numerous acyclic olefins can be run under ROCM reaction conditions to produce the desired high molecular weight products. Many of the products have good PDIs ranging from 1 to 2, which represent products that are useful in industrial applications.

What is claimed is:

1. A method for carrying out a catalytic ring-opening cross-metathesis reaction, comprising contacting
   (a) at least one olefinic substrate, wherein the olefinic substrate comprises an esterification product of an unsaturated fatty acid with an alcohol, with
   (b) at least one cyclic olefin as a cross metathesis partner, in the presence of
   (c) a ruthenium alkylidene olefin metathesis catalyst,
   (d) under conditions effective to allow ring insertion cross metathesis whereby the cyclic olefin is simultaneously opened and inserted into the olefinic substrate.

2. The method of claim 1, wherein the alcohol is a saturated alcohol.

3. The method of claim 2, wherein the saturated alcohol is monohydric.

4. The method of claim 2, wherein the saturated alcohol is dihydric or polyhydric.

5. The method of claim 4, wherein the saturated alcohol is selected from 1,2 dihydroxypropane and glycerol.

6. The method of claim 1, wherein the at least one olefinic substrate comprises a monoglyceride, a diglyceride, a triglyceride, or a mixture thereof.

7. The method of claim 1, wherein the unsaturated fatty acid comprises a seed oil.

8. The method of claim 6, wherein the olefinic substrate has the structure of formula (I)

(I)

wherein $R^V$, $R^{VI}$, and $R^{VII}$ are independently selected from hydrogen, $C_1$ to $C_{36}$ hydrocarbyl, $C_1$ to $C_{36}$ substituted hydrocarbyl, $C_1$ to $C_{36}$ heteroatom-containing hydrocarbyl, $C_1$ to $C_{36}$ substituted heteroatom-containing hydrocarbyl, and functional groups, provided that at least one of $R^V$, $R^{VI}$, and $R^{VII}$ is other than hydrogen and comprises an internal olefin.

9. The method of claim 8, wherein $R^V$, $R^{VI}$, and $R^{VII}$ are independently selected from $C_1$ to $C_{15}$ alkylene.

10. The method of claim 9, wherein $R^V$, $R^{VI}$, and $R^{VII}$ are independently selected from $C_4$ to $C_{12}$ alkylene.

11. The method of claim 8, wherein each of $R^V$, $R^{VI}$, and $R^{VII}$ is $C_1$ to $C_{36}$ hydrocarbyl containing zero to two double bonds and optionally substituted with one or two hydroxyl groups.

12. The method of claim 11, wherein each of $R^V$, $R^{VI}$, and $R^{VII}$ is $C_1$ to $C_{18}$ hydrocarbyl containing zero to two double bonds and optionally substituted with one or two hydroxyl groups.

13. The method of claim 1, wherein the cyclic olefin is an optionally substituted, optionally heteroatom-containing, mono-unsaturated, di-unsaturated, or poly-unsaturated $C_5$ to $C_{24}$ hydrocarbon.

14. The method of claim 13, wherein the cyclic olefin is a mono-unsaturated, diunsaturated, or poly-unsaturated $C_6$ to $C_{16}$ hydrocarbon optionally substituted with one or two hydroxyl groups and optionally containing an ester linkage.

15. The method of claim 14, wherein the cyclic olefin is mono-unsaturated, diunsaturated, or tri-unsaturated.

16. The method of claim 15, wherein the cyclic olefin is mono-unsaturated.

17. The method of claim 1, wherein the at least one cyclic olefin is a mixture of a cyclic olefinic hydrocarbon and a cyclic alkenol.

18. The method of claim 1, wherein the molar ratio of the olefinic substrate to the cyclic olefin is in the range of about 1:2 to about 1:10000.

19. The method of claim 18, wherein the molar ratio of the olefinic substrate to the cyclic olefin is in the range of about 1:5 to about 1:1000.

20. A method for carrying out a catalytic ring-opening cross-metathesis reaction, comprising contacting
   (a) at least one olefinic substrate, wherein the olefinic substrate comprises at least one unsaturated moiety, with (b) at least one cyclic olefin as a cross metathesis partner, in the presence of
(c) a ruthenium alkylidene olefin metathesis catalyst,
(d) under conditions effective to allow ring insertion cross metathesis whereby the cyclic olefin is simultaneously opened and inserted into the olefinic substrate,
wherein the at least one cyclic olefin is a mixture of a cyclic olefinic hydrocarbon and a cyclic alkenol, and
wherein the olefinic substrate, the cyclic olefinic hydrocarbon, and the cyclic alkenol are in a ratio of approximately 1:50:50.

21. A method for carrying out a catalytic ring-opening cross-metathesis reaction, comprising contacting
(a) at least one olefinic substrate, wherein the olefinic substrate comprises at least one unsaturated moiety, with
(b) at least one cyclic olefin as a cross metathesis partner, in the presence of
(c) a ruthenium alkylidene olefin metathesis catalyst,
(d) under conditions effective to allow ring insertion cross metathesis whereby the cyclic olefin is simultaneously opened and inserted into the olefinic substrate,
wherein the at least one cyclic olefin is a mixture of a cyclic olefinic hydrocarbon and a cyclic alkenol, and
wherein the molar ratio of the cyclic olefinic hydrocarbon to the cyclic alkenol is in the range of about 1:1 to about 1:100.

22. The method of claim 21, wherein the molar ratio of the cyclic olefinic hydrocarbon to the cyclic alkenol is in the range of about 1:1 to about 1:10.

23. A method for carrying out a catalytic ring-opening cross-metathesis reaction, comprising contacting
(a) at least one olefinic substrate, wherein the olefinic substrate comprises at least one unsaturated moiety, with
(b) at least one cyclic olefin as a cross metathesis partner, in the presence of
(c) a ruthenium alkylidene olefin metathesis catalyst,
(d) under conditions effective to allow ring insertion cross metathesis whereby the cyclic olefin is simultaneously opened and inserted into the olefinic substrate,
wherein the at least one cyclic olefin is a mixture of a cyclic olefinic hydrocarbon and a cyclic alkenol, and
wherein the molar ratio of the cyclic olefinic hydrocarbon to the cyclic alkenol is in the range of about 100:1 to about 1:1.

24. The method of claim 23, wherein the molar ratio of the cyclic olefinic hydrocarbon to the cyclic alkenol is in the range of about 10:1 to about 1:1.

25. The method of claim 1, wherein the contacting is carried out in an inert atmosphere.

26. A method for carrying out a catalytic ring-opening cross-metathesis reaction, comprising contacting
(a) at least one olefinic substrate, wherein the olefinic substrate comprises at least one unsaturated moiety, with
(b) at least one cyclic olefin as a cross metathesis partner, in the presence of
(c) a ruthenium alkylidene olefin metathesis catalyst,
(d) under conditions effective to allow ring insertion cross metathesis whereby the cyclic olefin is simultaneously opened and inserted into the olefinic substrate,
wherein the contacting is carried out in an oxygen-containing atmosphere.

27. The method of claim 1, wherein the catalyst is present in an amount that is less than about 1000 ppm relative to the olefinic substrate.

28. The method of claim 27, wherein the catalyst is present in an amount ranging from about 50 ppm to about 300 ppm relative to the olefinic substrate.

29. The method of claim 1, wherein the ruthenium alkylidene olefin metathesis catalyst has the structure of formula (II)

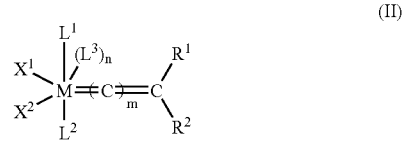

wherein:
M is ruthenium;
n is 0 or 1;
m is 0, 1, or 2;
$L^1$, $L^2$ and $L^3$ are neutral electron donor ligands;
$X^1$ and $X^2$ are anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups;
wherein any two or more of $X^1$, $X^2$, $L^1$, $L^2$, $L^3$, $R^1$, and $R^2$ can be taken together to form a cyclic group, and further wherein anyone of $X^1$, $X^2$, $L^1$, $L^2$, $L^3$, $R^1$, and $R^2$ can be attached to a support.

30. The method of claim 29, wherein:
n and m are 0;
$R^1$ is hydrogen, and $R^2$ is selected from $C_1$-$C_{20}$ alkyl, $C_2$-$C_{20}$ alkenyl, and $C_5$-$C_{20}$ aryl, optionally substituted with one or more moieties selected from $C_1$-$C_6$ alkyl, $C_1$-$C_6$ alkoxy, and phenyl;
$L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether; and
$X^1$ and $X^2$ are independently selected from hydrogen, halide, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_6$-$C_{20}$ aryloxycarbonyl, $C_2$-$C_{20}$ acyl, $C_2$-$C_{20}$ acyloxy, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of hydrogen and halide, are optionally further substituted with one or more groups selected from halide, $C_1$-$C_6$ alkyl, $C_1$-$C_6$ alkoxy, and phenyl.

31. The method of claim 29, wherein $L^1$ has the structure of formula (III)

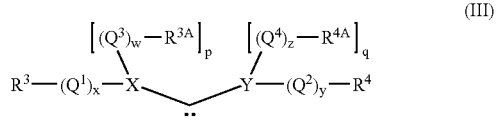

in which:
X and Y are heteroatoms selected from N, O, S, and P;
p is zero when X is O or S, and p is 1 when X is N or P;
q is zero when Y is O or S, and q is 1 when Y is N or P;
$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;
w, x, y, and z are independently zero or 1; and
$R^3$, $R^{3A}$, $R^4$, and $R^{4A}$ are independently selected from hydrogen, hydrocarbyl, substituted
hydrocarbyl, heteroatom-containing hydrocarbyl, and substituted heteroatom-containing hydrocarbyl, such that the transition metal complex is a ruthenium carbene complex having the
structure of formula (IV)

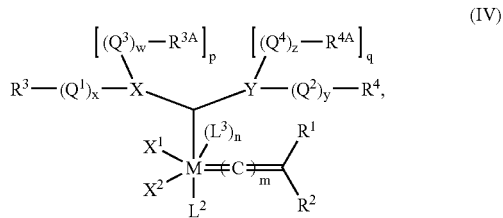

(IV)

wherein any two or more $X^1$, $X^2$, $L^2$, $L^3$, $R^1$, $R^2$, $R^3$, $R^{3A}$, $R^4$ and $R^{4A}$ can be taken together to form a cyclic group, and further wherein anyone or more of $X^1$, $X^2$, $L^2$, $L^3$, $R^1$, $R^2$, $R^3$, $R^{3A}$, $R^4$ and $R^{4A}$ may be attached to a support.

32. The method of claim 31, wherein m, w, x, y, and z are zero, X and Y are N, and $R^{3A}$ and $R^{4A}$ are linked to form -Q-, such that the ruthenium carbene complex has the structure of formula (VI)

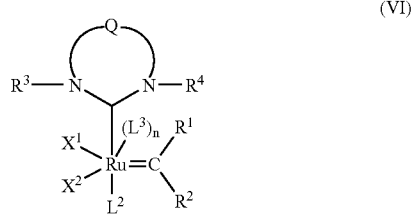

(VI)

wherein Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group.

33. The method of claim 32, wherein Q has the structure —$CR^{11}R^{12}$—$CR^{13}R^{14}$— or —$CR^{11}$=$CR^{13}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups, and or wherein any two of $R^{11}$, $R^{12}$, $R^{13}$, and $R^{14}$ may be linked together to form a substituted or unsubstituted, saturated or unsaturated ring.

34. The method of claim 33, wherein:
$R^1$ is hydrogen, and $R^2$ is selected from $C_1$-$C_{20}$ alkyl, $C_2$-$C_{20}$ alkenyl, and aryl, optionally substituted with one or more moieties selected from $C_1$-$C_6$ alkyl, $C_1$-$C_6$ alkoxy, and phenyl;
$L^2$ is selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether;
$X^1$ and $X^2$ are independently selected from hydrogen, halide, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl $C_6$-$C_{20}$ aryloxycarbonyl, $C_2$-$C_{20}$ acyl, $C_2$-$C_{20}$ acyloxy, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of hydrogen and halide, are optionally further substituted with one or more groups selected from halide, $C_1$-$C_6$ alkyl, $C_1$-$C_6$ alkoxy, and phenyl;
$R^3$ and $R^4$ are aromatic, substituted aromatic, heteroaromatic, substituted heteroaromatic, alicyclic, substituted alicyclic, heteroatom-containing alicyclic, or substituted heteroatom containing alicyclic, composed of from one to about five rings; and
$R^{12}$ and $R^{14}$ are hydrogen, and $R^{11}$ and $R^{13}$ are selected from hydrogen, lower alkyl and phenyl, or are linked to form a cyclic group.

35. The method of claim 1, wherein the catalyst is a Grubbs-Hoveyda complex.

36. The method of claim 35, wherein the complex has an N-heterocyclic carbene ligand associated with the ruthenium center.

37. The method of claim 1, wherein the cyclic olefin is functionalized.

* * * * *